(12) United States Patent
Taniguchi et al.

(10) Patent No.: US 12,033,610 B2
(45) Date of Patent: Jul. 9, 2024

(54) ACOUSTIC LENS, ULTRASOUND PROBE AND ULTRASOUND DIAGNOSTIC APPARATUS

(71) Applicant: KONICA MINOLTA, INC., Tokyo (JP)

(72) Inventors: Tetsuya Taniguchi, Tokyo (JP); Shuhei Okuda, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 384 days.

(21) Appl. No.: 17/529,385

(22) Filed: Nov. 18, 2021

(65) Prior Publication Data

US 2022/0189452 A1 Jun. 16, 2022

(30) Foreign Application Priority Data

Dec. 11, 2020 (JP) ................. 2020-205865

(51) Int. Cl.
 *A61B 8/00* (2006.01)
 *A61B 8/14* (2006.01)
 (Continued)

(52) U.S. Cl.
 CPC ............ *G10K 11/30* (2013.01); *B06B 1/0607* (2013.01)

(58) Field of Classification Search
 CPC ....... A61B 8/00; A61B 8/0841; A61B 8/4466; A61B 8/4494; A61B 8/44; A61B 8/4444;
 (Continued)

(56) References Cited

U.S. PATENT DOCUMENTS 5,083,568 A * 1/1992 Shimazaki ........... G10K 11/345
 600/459
5,865,750 A * 2/1999 Hatfield ................. A61B 8/065
 600/443
(Continued)

FOREIGN PATENT DOCUMENTS

JP S6079158 U * 6/1985
JP H02228952 A * 9/1990
(Continued)

OTHER PUBLICATIONS

Japanese Office Action (and an English language translation thereof) dated May 14, 2024, issued in counterpart Japanese Application No. 2020-205865.

*Primary Examiner* — Edgardo San Martin
(74) *Attorney, Agent, or Firm* — Holtz, Holtz & Volek PC

(57) ABSTRACT

Provided is an acoustic lens applied to an ultrasound probe and forming an ultrasound beam by focusing ultrasound transmitted from a piezoelectric transducer, in which: an ultrasound radiation surface of the acoustic lens includes: a first area that is located in a lens center portion and forms a focal point at a position corresponding to a deep portion of the ultrasound beam; and a second area that is located on a lens outer side of the first area and forms a focal point at a position corresponding to a shallow portion of the ultrasound beam, and a focal depth formed by a lens portion of each position of the first area and the second area draws a profile that becomes continuously shallow from a side of the lens center portion to the lens outer side.

9 Claims, 25 Drawing Sheets

(51) Int. Cl.
*B06B 1/06* (2006.01)
*G10K 11/30* (2006.01)

(58) Field of Classification Search
CPC .... A61B 8/4281; A61B 8/4272; G10K 11/30; G10K 11/26; G10K 11/18; B06B 1/0607; B06B 1/06; B06B 1/00
See application file for complete search history.

(56) References Cited

U.S. PATENT DOCUMENTS

| | | | |
|---|---|---|---|
| 6,618,206 B2 * | 9/2003 | Tarakci | G10K 11/30 600/459 |
| 7,263,888 B2 | 9/2007 | Barshinger et al. | |
| 8,366,616 B2 * | 2/2013 | Oshiki | G01S 7/52046 600/443 |
| 9,307,954 B2 * | 4/2016 | Nishigaki | A61B 8/4444 |
| 10,448,924 B2 * | 10/2019 | Fraser | G01S 7/52046 |
| 11,529,117 B2 * | 12/2022 | Taniguchi | G01S 7/52079 |
| 11,555,906 B2 * | 1/2023 | Song | A61B 8/00 |
| 11,744,555 B2 * | 9/2023 | Watanabe | A61B 8/14 600/437 |
| 11,841,315 B2 * | 12/2023 | Haji Reza | G01N 21/1702 |
| 2007/0197917 A1 * | 8/2007 | Bagge | G10K 11/30 600/459 |
| 2009/0043206 A1 * | 2/2009 | Towfiq | A61B 8/483 600/447 |
| 2011/0319768 A1 * | 12/2011 | Saito | G10K 11/30 600/472 |
| 2016/0058427 A1 * | 3/2016 | Nishigaki | A61B 8/4461 600/447 |
| 2016/0143619 A1 * | 5/2016 | Bae | A61B 8/461 600/459 |
| 2017/0209124 A1 * | 7/2017 | Gawazawa | A61B 8/0841 |
| 2019/0029644 A1 | 1/2019 | Nishigaki et al. | |
| 2022/0211345 A1 * | 7/2022 | Osawa | B06B 1/067 |

FOREIGN PATENT DOCUMENTS

| | | | |
|---|---|---|---|
| JP | H03123541 A | * | 5/1991 |
| JP | 2001212146 A | | 8/2001 |
| JP | 2004024464 A | * | 1/2004 |
| JP | 2008228873 A | * | 10/2008 |
| JP | 2014004269 A | | 1/2014 |
| JP | 2019024777 A | | 2/2019 |
| JP | 2020130947 A | * | 8/2020 |

* cited by examiner

| | NEAR CENTER FOCAL DISTANCE (mm) | NEAR CENTER CONVERSION F VALUE | SHORTEST FOCAL DISTANCE (mm) | MINIMUM F VALU | F VALUE RATIO | OUTERMOST END SECTIONAL SHAPE | CTR VALUE (dB) AT EACH DEPTH | | | | | MI VALUE | Penetration (cm) | ACCUMULATION OF GEL AIR BUBBLES |
| | | | | | | | 1cm | 2cm | 3cm | 4cm | 5cm | TOTAL | | | |
|---|---|---|---|---|---|---|---|---|---|---|---|---|---|---|---|
| COMPARATIVE EXAMPLE 1 | 20.2 | 5.0 | 20.2 | 5.0 | 1.0 | CIRCULAR ARC | 7.5 | 8.0 | 6.4 | 1.2 | 0.6 | 23.8 | 1.6 | 5.2 | NO |
| COMPARATIVE EXAMPLE 2 | 59.8 | 15.0 | 59.8 | 15.0 | 1.0 | CIRCULAR ARC | 4.8 | 5.6 | 6.5 | 5.6 | 2.9 | 25.4 | 1.0 | 6.0 | NO |
| COMPARATIVE EXAMPLE 3 | 16.5 | 4.1 | 16.5 | 8.2 | 0.5 | CIRCULAR ARC | 4.4 | 6.6 | 7.6 | 5.8 | 3.0 | 27.4 | 1.1 | 6.2 | YES |
| COMPARATIVE EXAMPLE 4 | 18.2 | 4.6 | 17.9 | 9.8 | 0.5 | CONCAVE CURVED LINE | 4.2 | 7.0 | 7.3 | 5.4 | 3.0 | 26.9 | 1.1 | 6.0 | NO |
| PRESENT APPLICATION | 69.0 | 17.2 | 24.3 | 6.8 | 2.5 | STRAIGHT LINE | 6.2 | 7.3 | 7.6 | 5.6 | 3.4 | 30.1 | 1.4 | 6.4 | NO |

FIG. 21

ACOUSTIC LENS, ULTRASOUND PROBE AND ULTRASOUND DIAGNOSTIC APPARATUS

CROSS REFERENCE TO RELATED APPLICATIONS

The entire disclosure of Japanese Patent Application No. 2020-205865 filed on Dec. 11, 2020 is incorporated herein by reference in its entirety.

BACKGROUND

Technological Field

The present disclosure relates to an acoustic lens, an ultrasound probe and an ultrasound diagnostic apparatus.

Description of the Related Art

Ultrasound diagnostic apparatuses have been known which transmits ultrasound toward a subject, receives waves reflected by the subject and performs predetermined signal processing on the reception signal to visualize a shape, conditions or a behavior of the inside of the subject in the form of a tomographic image (e.g., see Japanese Patent Application Laid Open NO. 2019-024777). Such ultrasound diagnostic apparatuses can obtain a tomographic image with a simple operation of applying an ultrasound probe to a body surface or inserting the ultrasound probe into the body and thus is safe and puts a smaller burden on the subject.

Ultrasound diagnostic apparatuses are used also for performing diagnosis of a body tissue by inserting a puncture needle into a body of the patient as a subject to collect a tissue and/or body fluid, and for performing treatment with the puncture needle. In such diagnosis or treatment, an operator, for example, a doctor can perform puncturing while confirming a position of the puncture needle and a position of a part to be punctured (target) by visually recognizing the ultrasound image obtained by the ultrasound diagnostic apparatus. Incidentally, the puncture needle includes a medical needle and a medical device such as a catheter configured to be inserted into the subject.

Incidentally, this type of ultrasound diagnostic apparatus is required to ensure a wide depth of field and high spatial resolution such that a user is able to accurately recognize a position of the puncture needle and a position of the target from an ultrasound image.

One means to solve such a problem is to optimize the shape of an acoustic lens of an ultrasound probe. Specifically, when the acoustic lens can convert the ultrasound radiated from a piezoelectric transducer into an ultrasound beam that is uniformly and thinly focused over a wide range from a shallow portion to a deep portion, it is possible to improve a signal-to-noise (S/N) ratio of the ultrasound echo from each depth position of the subject in a depth direction, and thus, a wide depth of field and high spatial resolution are ensured.

Accordingly, in order to form the ultrasound beam that is uniformly and thinly focused over a wide range from the shallow portion to the deep portion, the inventors of the present application have studied an acoustic lens having a shape in which an inner area forms a focal point at the shallow portion and an outer area forms a focal point at the deep portion by designing an ultrasound radiation surface of the acoustic lens separately into the inner area located at a center portion of the lens (hereinafter may be referred to as a "lens center portion") and the outer area located on an outer side of the lens (hereinafter may be referred to as a "lens outer side") along a slice direction.

However, such an acoustic lens faces the problem in that a beam tail (or transverse tail of beam) is formed in the shallow portion and thus spatial resolution in the shallow portion in an ultrasound image is deteriorated (described later with reference to FIG. 7).

SUMMARY

The present disclosure has been made in view of the above-described problems, and an object thereof is to provide an acoustic lens, an ultrasound probe, and an ultrasound diagnostic apparatus each capable of generating an ultrasound image having a wide depth of field and high spatial resolution.

To achieve at least one of the abovementioned objects, according to an aspect of the present invention, an acoustic lens reflecting one aspect of the present invention is applied to an ultrasound probe and forms an ultrasound beam by focusing ultrasound transmitted from a piezoelectric transducer, the acoustic lens including:

an ultrasound radiation surface of the acoustic lens includes: a first area that is located in a lens center portion and forms a focal point at a position corresponding to a deep portion of the ultrasound beam; and a second area that is located on a lens outer side of the first area and forms a focal point at a position corresponding to a shallow portion of the ultrasound beam, and a focal depth formed by a lens portion of each position of the first area and the second area draws a profile that becomes continuously shallow from a side of the lens center portion to the lens outer side.

To achieve at least one of the abovementioned objects, according to another aspect of the present invention, an ultrasound probe reflecting one aspect of the present invention includes the above-described acoustic lens.

To achieve at least one of the abovementioned objects, according to another aspect of the present invention, an ultrasound diagnostic apparatus reflecting one aspect of the present invention includes the above-described ultrasound probe.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIG. 21 illustrates results of performance evaluations of acoustic lenses according to, respectively, the present application, related art 1, and related art 2 from the three perspectives of "Clutter Energy to Total Energy Ratio (CTR) (db)," "Penetration (cm)," and "accumulation of Gel air bubbles;"

DETAILED DESCRIPTION OF EMBODIMENTS

Hereinafter, one or more embodiments of the present invention will be described with reference to the drawings. However, the scope of the invention is not limited to the disclosed embodiments.

Overall Configuration of Ultrasound Diagnostic Apparatus

Figure 1:
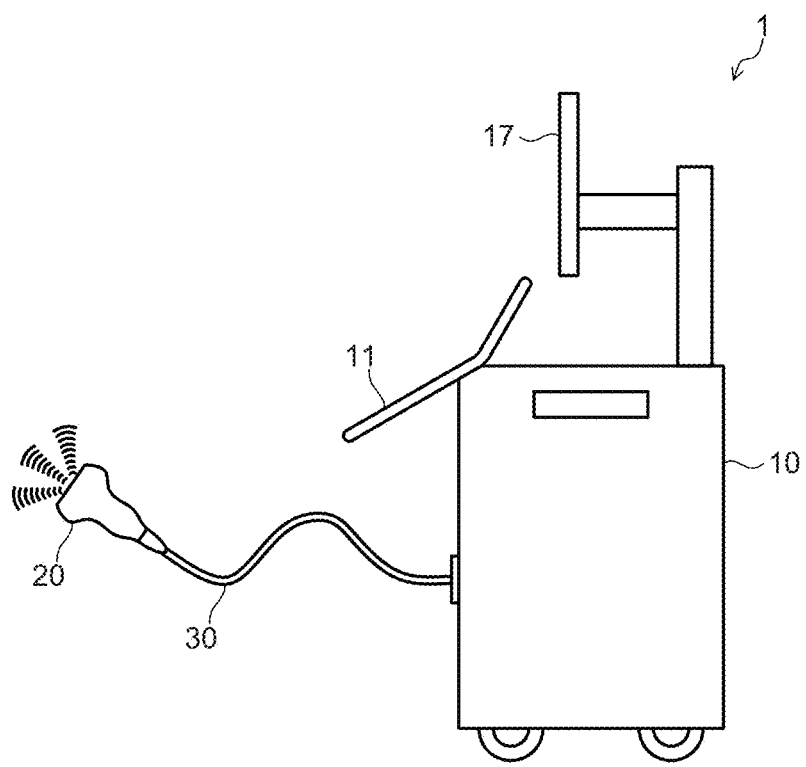
FIG. 1 illustrates an example of an external appearance of an ultrasound diagnostic apparatus.
Figure 2A:
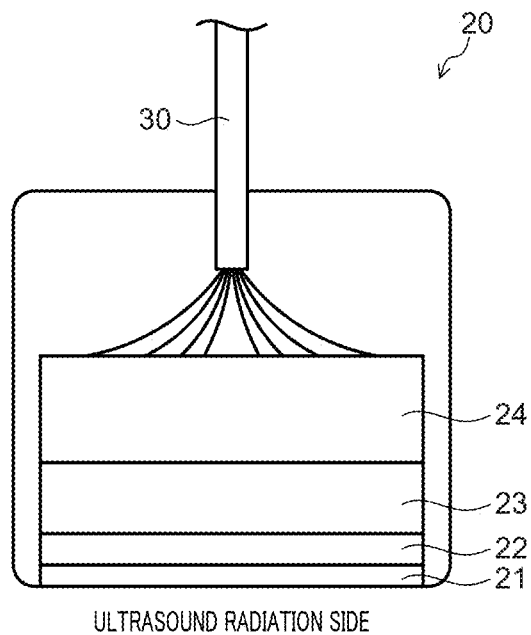
FIG. 2A and FIG. 2B illustrate an example of a configuration of an ultrasound probe.
Figure 2B:
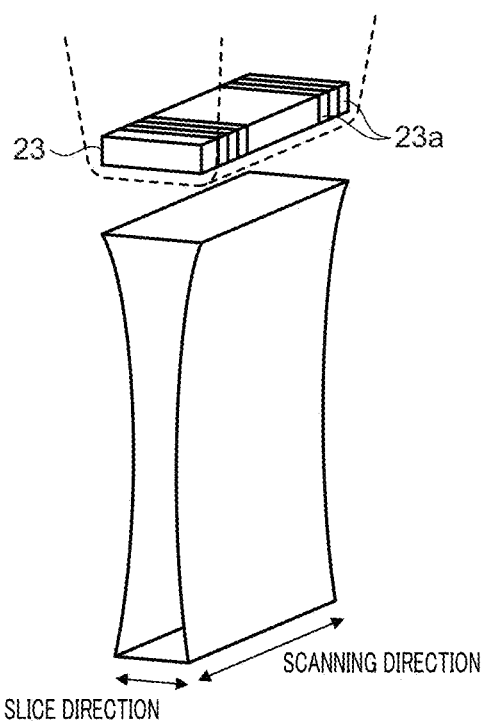

FIG. 1 illustrates an example of an external appearance of ultrasound diagnostic apparatus 1. FIG. 2A and FIG. 2B illustrate an example of a configuration of ultrasound probe 20. Note that, FIG. 2A is a plan view of ultrasound probe 20, and FIG. 2B is a perspective view of ultrasound probe 20.

Figure 3:
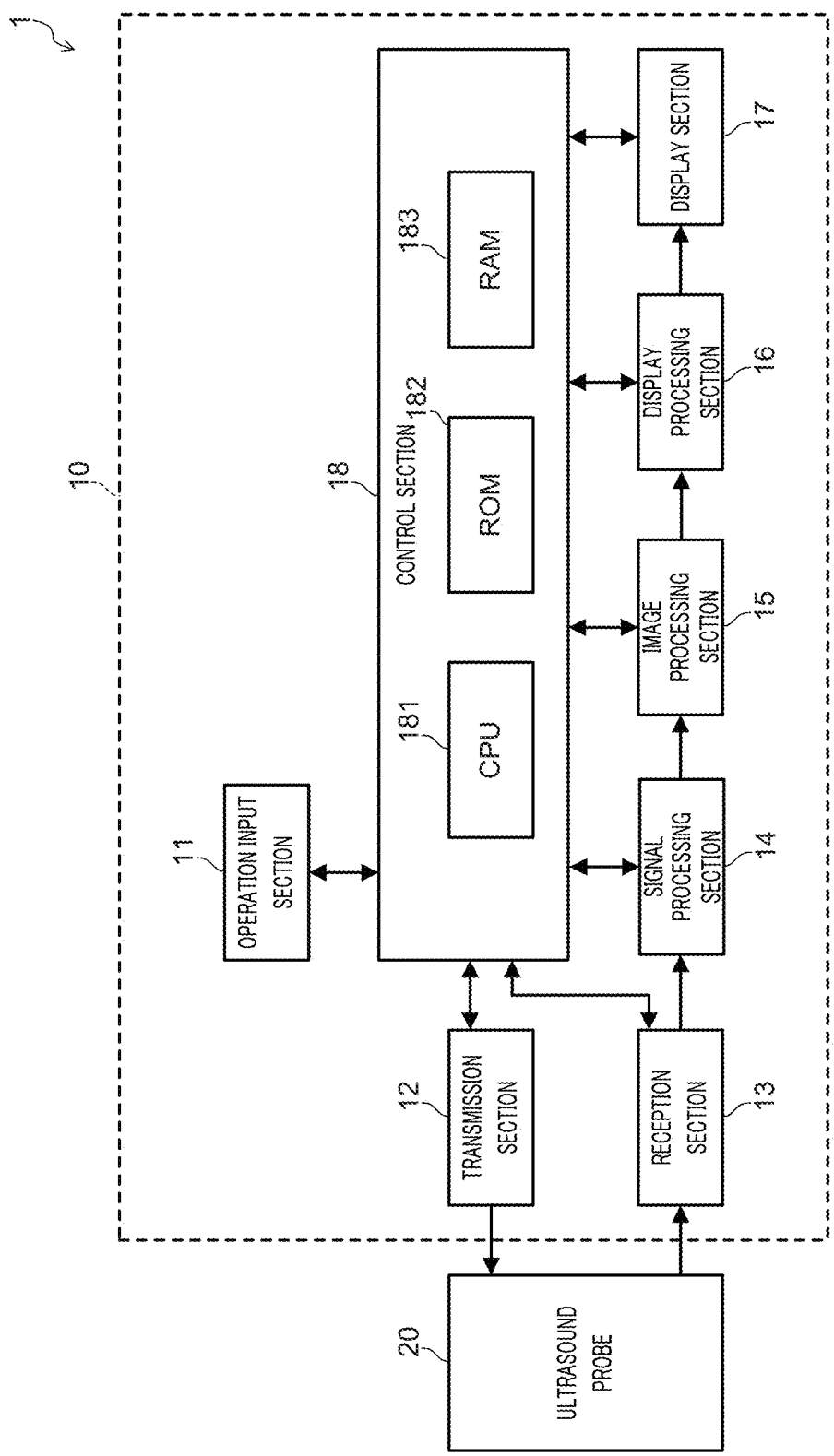
FIG. 3 is a block diagram illustrating a configuration example of a main part of a control system of the ultrasound diagnostic apparatus.

FIG. 3 is a block diagram illustrating a configuration example a main part of a control system of the ultrasound diagnostic apparatus 1.

As illustrated in FIG. 1, ultrasound diagnostic apparatus 1 includes ultrasound diagnostic apparatus body 10 and ultrasound probe 20. Ultrasound diagnostic apparatus body 10 and ultrasound probe 20 are connected with each other through cable 30.

Ultrasound diagnostic apparatus 1 is used for image diagnosis by visualizing the shape, conditions or behavior of an inside of a subject as an ultrasound image By way of example, in a puncture procedure of a puncture needle to a target (e.g., an extraction object of a sample such as a muscle, a tendon, a nerve fascicle, a tumor and the like of a subject), ultrasound diagnostic apparatus 1 is used by a user to check a position of the puncture needle or a position of a part to be punctured (target).

Ultrasound probe 20 transmits ultrasound to a subject and receives an ultrasound echo reflected by the subject. Ultrasound probe 20 converts the ultrasound echo into a reception signal and transmits it to ultrasound diagnostic apparatus body 10. Ultrasound probe 20 may be any electronic scanning probe such as a convex probe, a linear probe, and a sector probe, or a mechanical scanning probe such as a mechanical sector probe.

Ultrasound probe 20 includes acoustic lens 21, acoustic matching layer 22, transducer array 23, and bucking material 24 in this order from the ultrasound radiation side (see FIG. 2A). Note that, a protective layer may be further disposed on a surface (ultrasound radiation surface) side of acoustic lens 21.

Acoustic lens 21 focuses the ultrasound in a slice direction (a direction orthogonal to a scanning direction in which a plurality of transducers are arranged) to form an ultrasound beam. Acoustic lens 21 according to the present embodiment is made of a material having a slower sound speed than a living body (e.g., silicone resin), and has an arch shape in which a center portion thereof in the slice direction protrudes (i.e., substantially semi-cylindrical shape). However, the shape of an ultrasound radiation surface of acoustic lens 21 according to the present embodiment is not uniformly spherical while having a shape including a spherical shape and an aspherical shape in combination so that desired lens properties can be obtained (described later with reference to FIG. 8A).

Acoustic matching layer 22 is an intermediate substance intended for efficiently transmitting ultrasound into the subject, and performs matching between acoustic impedances of piezoelectric transducers 23a and the subject.

Transducer array 23 is not separated in the slice direction and is composed of a plurality of belt-shaped piezoelectric transducers 23a aligned in a single line in the scanning direction. That is, ultrasound probe 20 is a so-called single-line probe (also called a 1 D type probe).

Bucking material 24 attenuates unnecessary vibrations generated at transducer array 23.

Ultrasound probe 20 provides a beam profile of ultrasound that focuses in the slice direction (see FIG. 2B). Note that, focusing of ultrasound in the scanning direction may be achieved by driving piezoelectric transducers 23a in a switching manner (so-called electron scanning system).

Ultrasound diagnostic apparatus body 10 visualizes an internal state of the subject in the form of an ultrasound image (B mode image) by using a reception signal from ultrasound probe 20.

As illustrated in FIG. 3, ultrasound diagnostic apparatus body 10 includes operation input section 11, transmission section 12, reception section 13, signal processing section 14, image processing section 15, display processing section 16, display section 17, control section 18 and the like.

Transmission section 12, reception section 13, signal processing section 14, image processing section 15 and display processing section 16, which achieve respective functions in conjunction with control section 18, are composed of dedicated or general-purpose hardware (electronic circuit), such as a digital signal processor (DSP), an application specific integrated circuit (ASIC), and a programmable logic device (PLD), in accordance with respective processes.

Operation input section 11 receives an instruction command to start a diagnosis and the like, or input of information relating to the subject, for example. Operation input section 11 includes an operation panel having a plurality of input switches, a keyboard, a mouse and the like, for example. Note that, operation input section 11 may be composed of a touchscreen integrated with display section 17.

Under the instruction of control section 18, transmission section 12 generates a transmission signal (drive signal) and outputs it to ultrasound probe 20. Although not illustrated, transmission section 12 is configured to include a clock generation circuit, a pulse generation circuit, a pulse width setting section and a delay circuit, for example.

The clock generation circuit generates a clock signal that sets the transmission timing and/or the transmission frequency of a pulse signal. The pulse generation circuit generates a bipolar rectangular wave pulse of a preliminarily set voltage amplitude at a predetermined cycle. The pulse width setting section sets the pulse width of the rectangular wave pulse output from the pulse generation circuit. The rectangular wave pulse generated by the pulse generation circuit is separated into different wiring paths for respective piezoelectric transducers 23a of ultrasound probe 20 before or after the input to the pulse width setting section. The delay circuit delays the generated rectangular wave pulses in accordance with the transmission timings of respective piezoelectric transducers 23a, and outputs the resultant rectangular wave pulses to piezoelectric transducers 23a.

Under the instruction of control section 18, reception section 13 receives the reception signal from ultrasound probe 20 and outputs it to image processing section 15. Although not illustrated, reception section 13 is configured to include an amplifier, an A/D conversion circuit, and a phasing addition circuit, for example.

The amplifier amplifies, using a preliminarily set amplification factor, the reception signal according to the ultrasound received by each of piezoelectric transducers 23a of ultrasound probe 20. The A/D conversion circuit converts the amplified reception signal into digital data at a predetermined sampling frequency. The phasing addition circuit gives, to the A/D converted reception signal, a delay time for each wiring path corresponding to each piezoelectric transducer 23a to rectify the time phase, and performs addition (phasing addition) of them.

Signal processing section 14 performs a harmonic wave extracting process or the like as needed from the sound ray data input from reception section 13, detects (envelope detection) the extracted harmonic wave and thereby obtains a signal. In addition, signal processing section 14 performs processes such as logarithmic amplification, filtering (e.g., low-pass transmission, smoothing) and enhancement as needed.

Image processing section 15 generates a diagnostic image based on the reception signals obtained from signal processing section 14. Image processing section 15, for example, as one of the diagnostic images, generates a tomographic image representing, by a luminance signal corresponding to a signal strength of the reception signal, a two-dimensional structure in a cross section including a transmission direction of the signal (a depth direction of the subject) and a scanning direction of the ultrasound.

Image processing section 15 may include a storage section (e.g., Dynamic Random Access Memory (DRAM)) that stores diagnostic image data for the last predetermined number of frames in units of frames or a processing section that identifies a position of the puncture needle from the diagnostic image data and colors the identified puncture needle. As a method for identifying the position of the puncture needle, see, for example, Japanese Patent Application Laid Open No. 2014-212922 and Japanese Patent Application Laid Open No. 2020-010753, which are prior applications of the applicant of the present application (which are applications filled by the applicant of the present application prior to the filing the present application).

Under the instruction of control section 18, display processing section 16 converts the tomographic image data generated by image processing section 15 into a display signal corresponding to display section 17, and outputs as display image data.

Display section 17 is composed of, for example, a liquid crystal display, an organic EL display, or a CRT display. Under the instruction of control section 18, display section 17 displays the display image data obtained from display processing section 16.

Control section 18 controls the entirety of ultrasound diagnostic apparatus 1 by controlling operation input section 11, transmission section 12, reception section 13, signal processing section 14, image processing section 15, display processing section 16 and display section 17 in accordance with their functions.

Control section 18 includes a central processing unit (CPU) 181 as a computation/control device, a read only memory (ROM) 182 and random access memory (RAM) 183 as a main storage device and the like. ROM 182 stores a basic program and/or basic setting data. CPU 181 reads a program corresponding to processing content from ROM 182 and loads it in RAM 183, and, executes the loaded program so as to perform central control of the operations of functional blocks (transmission section 12, reception section 13, signal processing section 14, image processing section 15, display processing section 16, and display section 17) of ultrasound diagnostic apparatus body 10.

Configuration of Acoustic Lens

Next, an example of a configuration of acoustic lens 21 will be described.

First, with reference to FIGS. 4A and 4B to FIGS. 8A and 8B, a description will be given of a background which has lead the inventors of the present application to a configuration of acoustic lens 21 of ultrasound probe 20 of the present application.

Conventionally, acoustic lenses whose ultrasound radiation surfaces have spherical shapes have been adopted as an acoustic lens of ultrasound probe 20 (hereinafter referred to as "acoustic lens 21X according to related art 1"). However, acoustic lens 21X according to related art 1 focuses the ultrasound radiated from each position within the surface of the ultrasound radiation surface of acoustic lens 21X to a single point; hence, when an ultrasound beam is formed by using such acoustic lens 21X, a S/N ratio of an ultrasound echo from an object present at a depth position away from the focal depth position (e.g., a puncture needle and a target) is significantly deteriorated.

Accordingly, the inventors of the present application have studied an acoustic lens having an shape in which inner area 21Ya forms a focal point at the shallow portion and outer area 21Yb forms a focal point at the deep portion by designing an ultrasound radiation surface of the acoustic lens of ultrasound probe 20 separately into inner area 21Ya located at a lens center portion and outer area 21Yb located at an outer side of the lens of inner area 21Ya, along a slice direction (hereinafter referred to as "acoustic lens 21Y according to related art 2").

Figure 4A:
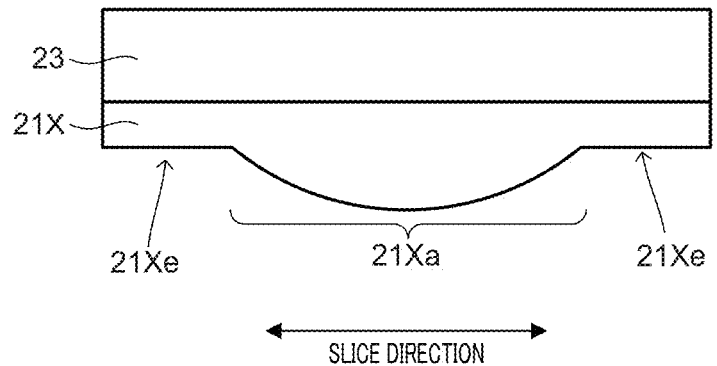
FIG. 4A and FIG. 4B illustrate an example of a shape of an acoustic lens according to related art 1.
Figure 4B:
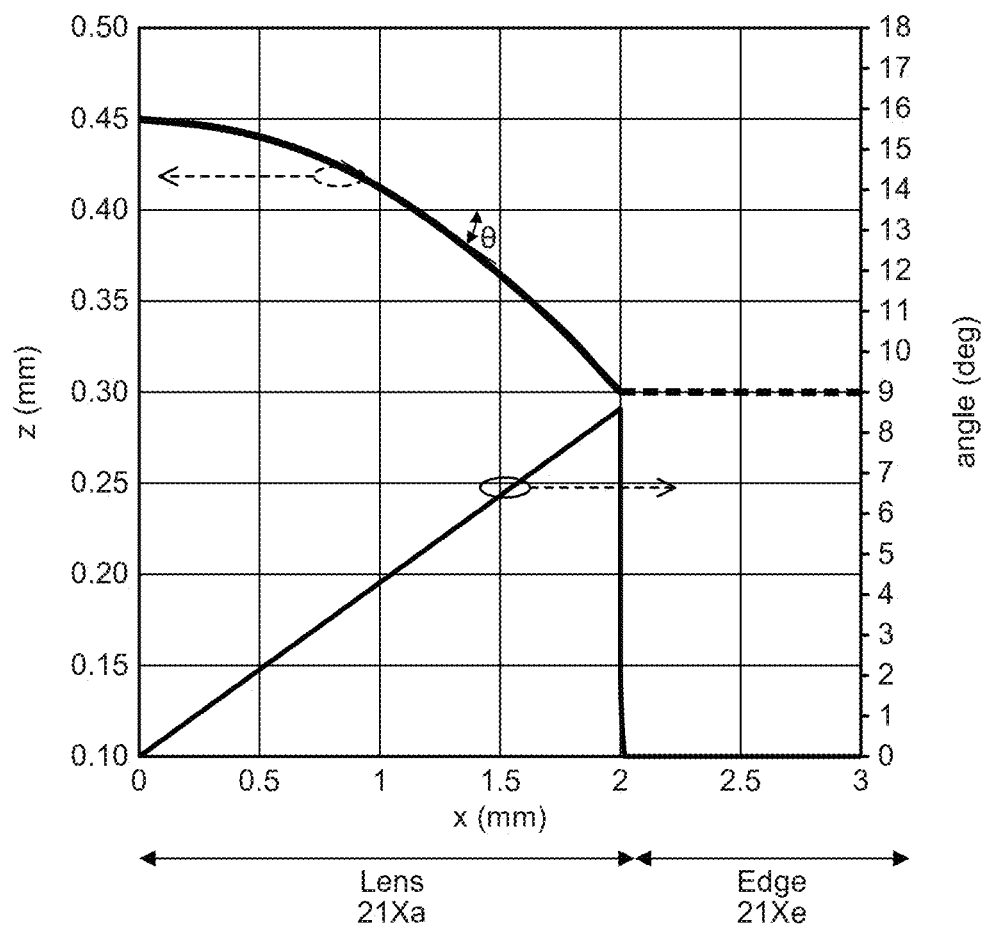
Figure 5A:
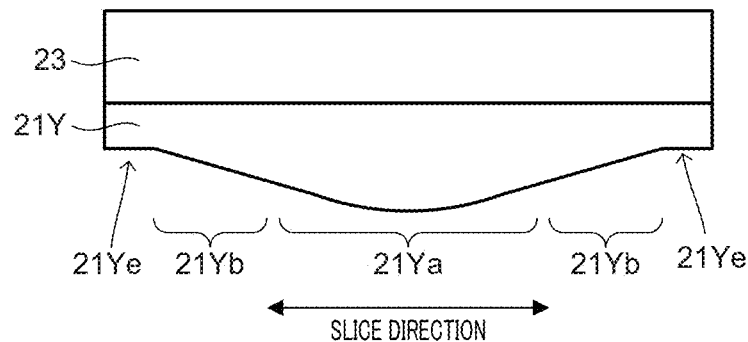
FIG. 5A and FIG. 5B illustrate an example of a shape of an acoustic lens according to related art 2.
Figure 5B:
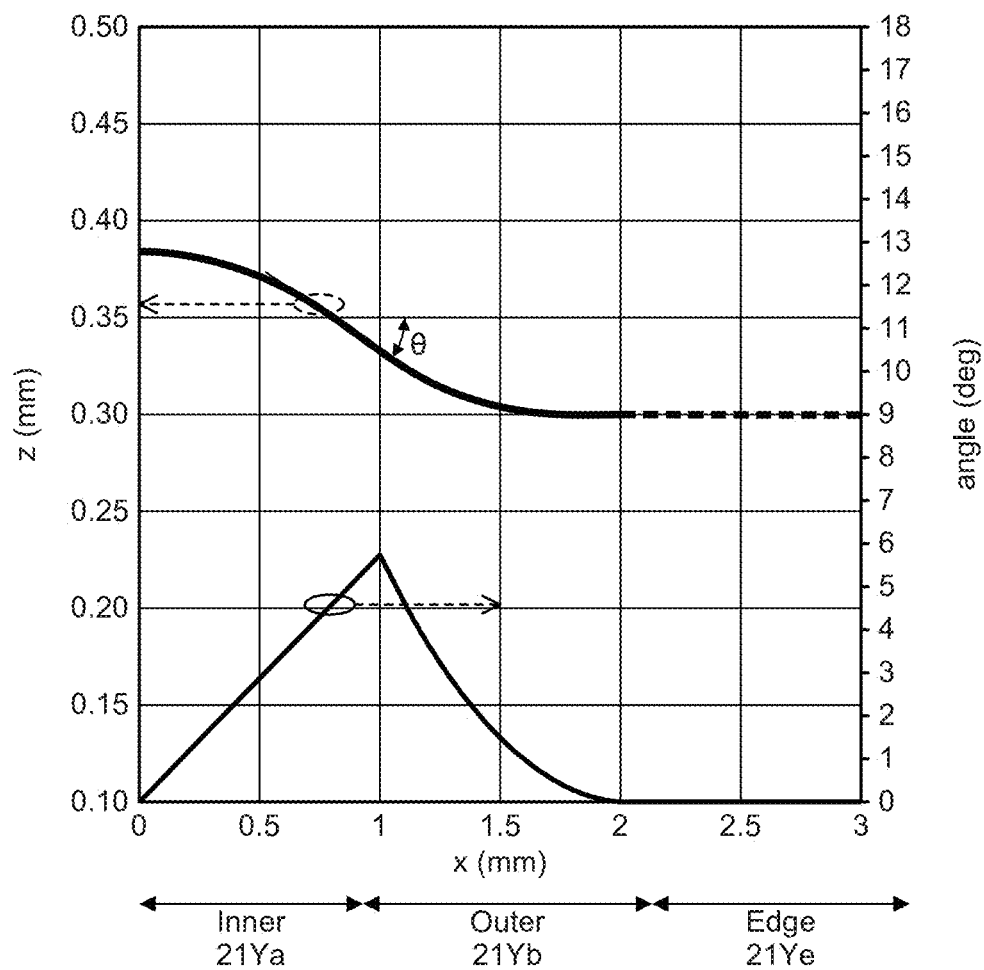
Figure 6:
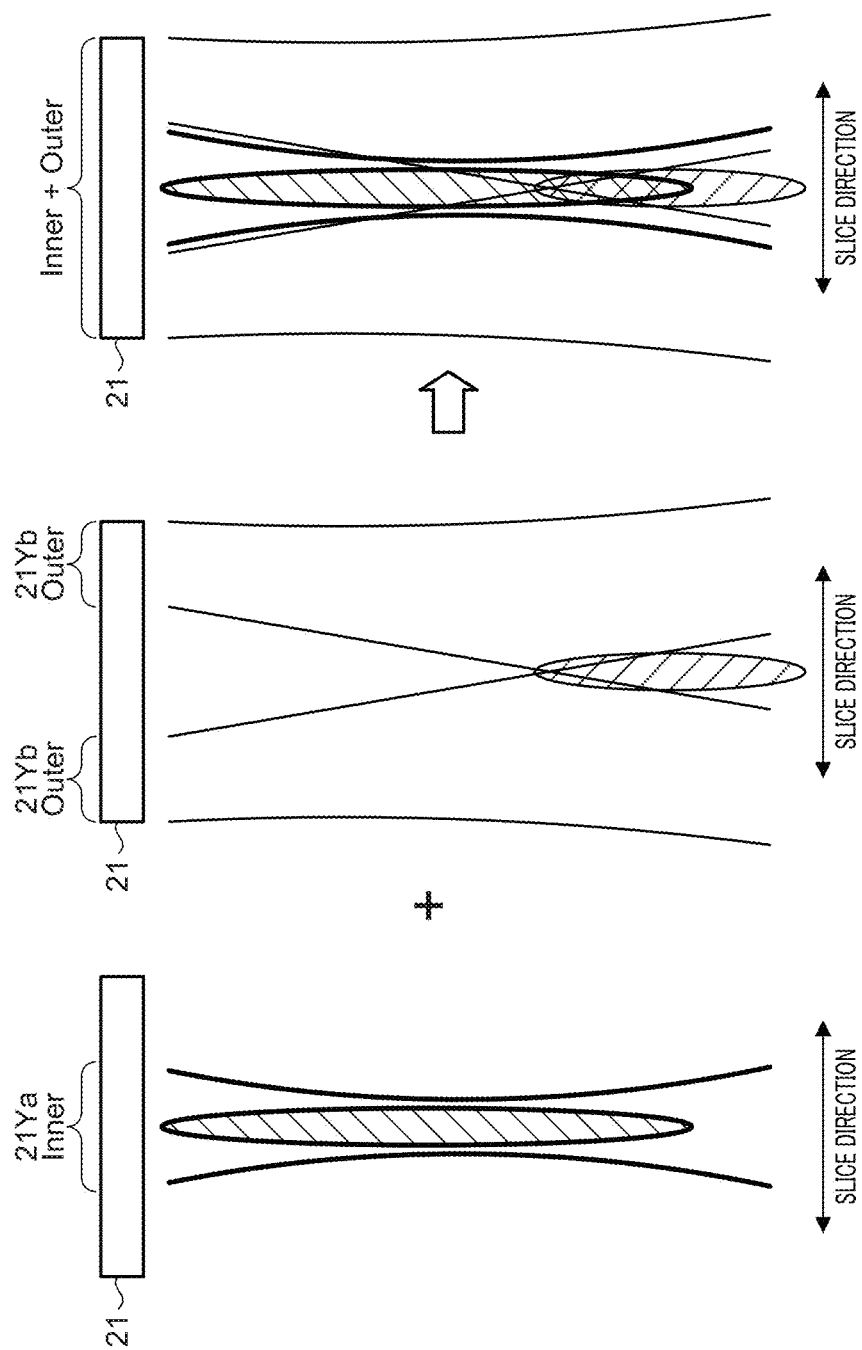
FIG. 6 describes a design concept of the acoustic lens according to related art 2.

FIG. 4A and FIG. 4B illustrate an example of a shape of acoustic lens 21X according to related art 1. FIG. 5A and FIG. 5B illustrate an example of a shape of acoustic lens 21Y according to related art 2. FIG. 6 describes a design concept of acoustic lens 21Y according to related art 2.

In FIGS. 4A, 4B, 5A and 5B, the upper diagrams (FIG. 4A and FIG. 5A) schematically illustrate shapes of acoustic lenses 21X and 21Y, respectively, whereas the lower diagrams (FIG. 4B and FIG. 5B) schematically illustrate detailed shapes of ultrasound radiation surfaces of acoustic lenses 21X and 21Y, respectively.

The upper graphs of FIGS. 4B and 5B indicate coordinates of each position within the surfaces of the ultrasound radiation surfaces of acoustic lenses 21X and 21Y with a two-dimensional coordinate system in which the slice direction is an x-axis (with a lens center as a zero point, an x-axis plus direction corresponds to a lens outer direction) and an ultrasound radiation direction is a y-axis (hereinafter also referred to as "shape profile of the ultrasound radiation surface of the acoustic lens"). In addition, the lower graphs of FIGS. 4B and 5B indicate coordinates of a tangent angle of each position in the surfaces of the ultrasound radiation surfaces of acoustic lenses 21X and 21Y (as illustrated in FIGS. 4B and 5B with $\theta$, a tangent angle means an inclination angle that a tangent has with respect to the x-axis when the tangent is drawn with respect to each position of the shape profiles of ultrasound radiation surfaces of acoustic lenses 21X and 21Y; hereinafter the same) with a two-dimensional coordinate system in which the slice direction is an x-axis and a value of the tangent angle as a y-axis (hereinafter, also referred to as "tangent angle profile of the ultrasound radiation surface of the acoustic lens").

Incidentally, in a case where the ultrasound radiation surface has a spherical shape, the tangent angle profile takes a constant value for an inclination of the tangent angle ($=d\theta/dx$) towards the x-axis plus direction, as illustrated in 4B. This means that, in the tangent angle profile, the ultrasound radiation surface has a shape in which a curvature gradually increases from a center side of the lens to an outer side of the lens in a case where the inclination of the tangent angle ($=d\theta/dx$) increases towards the x-axis plus direction, whereas the ultrasound radiation surface has a shape in which the curvature gradually decreases from the center side of the lens to the outer side of the lens in a case where the inclination of the tangent angle ($=d\theta/dx$) decreases towards the x-axis plus direction.

Figure 8A:
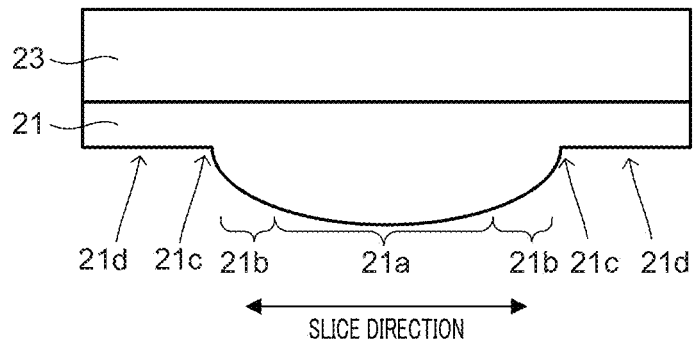
FIG. 8A and FIG. 8B illustrate an example of a shape of an acoustic lens according to an embodiment of the present invention.

Acoustic lens 21X according to related art 1 includes lens portion 21Xa having a spherical shape, as illustrated in FIG. 4A. Incidentally, edge area 21Xe illustrated in FIG. 4A is a flat surface of the outermost end of acoustic lens 21X, provided for the purpose of, for example, making a satisfactory contact state between the living body and acoustic lens 21X. Edge area 21Xe is not specifically mentioned in the following because it is located at the outermost end or outside of piezoelectric transducer 23a and has no significant impact on beam properties of the ultrasound beams formed by acoustic lens 21X. In other words, edge area 21Xe may be omitted in constituting acoustic lens 21X. Note that, edge area 21Ye illustrated in FIG. 5A and edge area 21d illustrated in FIG. 8A are the same in this point.

Acoustic lens 21Y according to related art 2 is set so that, for example, inner area 21Ya has a spherical shape, and outer area 21Yb has an inclined shape, as illustrated in FIG. 5A. That is, in the ultrasound radiation surface of acoustic lens 21Y according to related art 2, the curvature is different between inner area 21Ya and outer area 21Yb, and the curvature of inner area 21Ya is larger than the curvature of outer area 21Yb. Thus, in acoustic lens 21Y according to related art 2, focusing properties of ultrasound of inner area 21Ya becomes lower than that of outer area 21Yb.

With such a configuration, acoustic lens 21Y according to related art 2 focuses the ultrasound radiated from inner area 21Ya at a shallow position (see an area with diagonal lines in the left diagram of FIG. 6) and focuses the ultrasound radiated from outer area 21Yb at a deep position (see an area with diagonal lines in the central diagram of FIG. 6). That is, in acoustic lens 21Y according to related art 2, the ultrasound radiated from inner area 21Ya supports the central axis sound pressure of the shallow portion of the ultrasound beam (represents the sound pressure of the lens center axis in the slice direction of acoustic lens 21Y; hereinafter the same), and the ultrasound radiated from outer area 21Yb supports the central axis sound pressure of the deep portion of the ultrasound beam.

As a result, the ultrasound beam formed by acoustic lens 21Y according to related art 2 can be made more focused over a wide range from the shallow portion to the deep portion than the ultrasound beam formed by acoustic lens 21X according to related art 1.

However, intensive studies by the inventors of the present application have revealed that, in an ultrasound beam formed using acoustic lens 21Y according to related art 2, the ultrasound radiated from outer area 21Yb is superimposed on the ultrasound radiated from inner area 21Ya at the shallow portion in practice, resulting in forming of the beam tails (or transvers tails of beam). In other words, in the ultrasound beam formed using acoustic lens 21Y according to related art 2, a beam width becomes spread in the slice direction in the shallow portion. Such beam tails cause degradation of spatial resolution in the shallow portion of an ultrasound image. Note that, it is presumed that the beam tails are generated by diffuse broadening components of the ultrasound radiated from outer area 21Yb.

Figure 7:
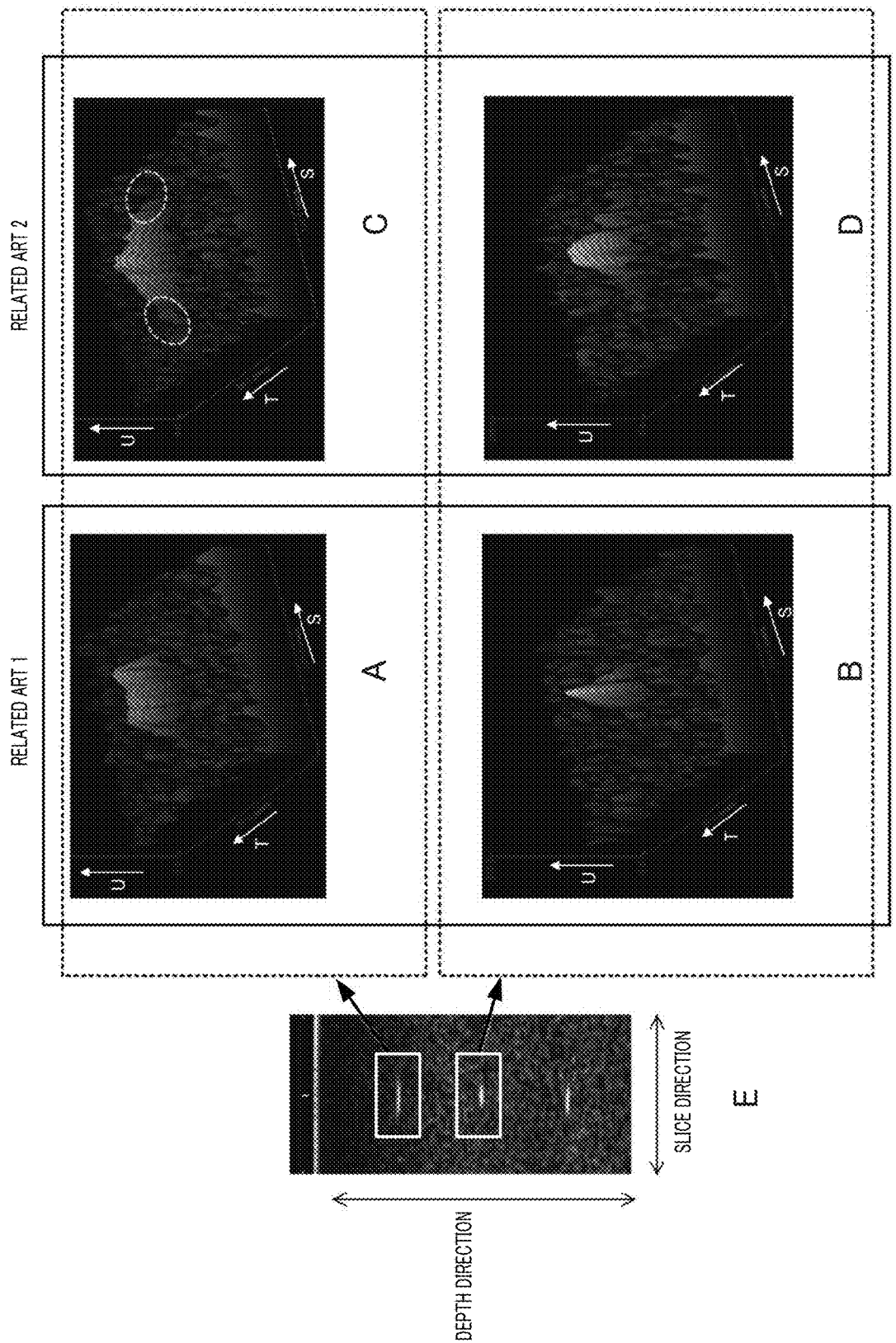
FIG. 7 illustrates examples of beam tails generated in an ultrasound beam formed by the acoustic lens according to related art 2.

FIG. 7 illustrates examples of beam tails generated in an ultrasound beam formed by acoustic lens 21Y according to related art 2.

Part A and part B of FIG. 7 illustrate examples of acoustic energy distribution related to imaging of the shallow portion of the ultrasound beam formed by acoustic lens 21X according to related art 1, and part C and part D of FIG. 7 illustrate examples of the acoustic energy distribution of the shallow portion of the ultrasound beam formed by acoustic lens 21Y according to related art 2. In part A to part D of FIG. 7, an S-axis represents the slice direction, a T-axis represents the scanning direction, and a U-axis represents an acoustic energy value of the ultrasound beam (here, a value converted from luminance information of the ultrasound image to the acoustic energy value). Part E of FIG. 7 illustrates depth positions from which data of part A to part D of FIG. 7 have been collected.

In particular, as can be seen by comparison between part C and part A of FIG. 7, in the ultrasound beam formed by acoustic lens 21Y according to related art 2, the beam tails are generated at the shallow portion of the ultrasound beam.

Acoustic lens 21 of the present invention is designed in view of the above problems of acoustic lens 21X according to related art 1 and acoustic lens 21Y according to related 2.

Hereinafter, with reference to FIGS. 8A and 8B to FIG. 11, a configuration of acoustic lens 21 according to an embodiment will be described.

Figure 8B:
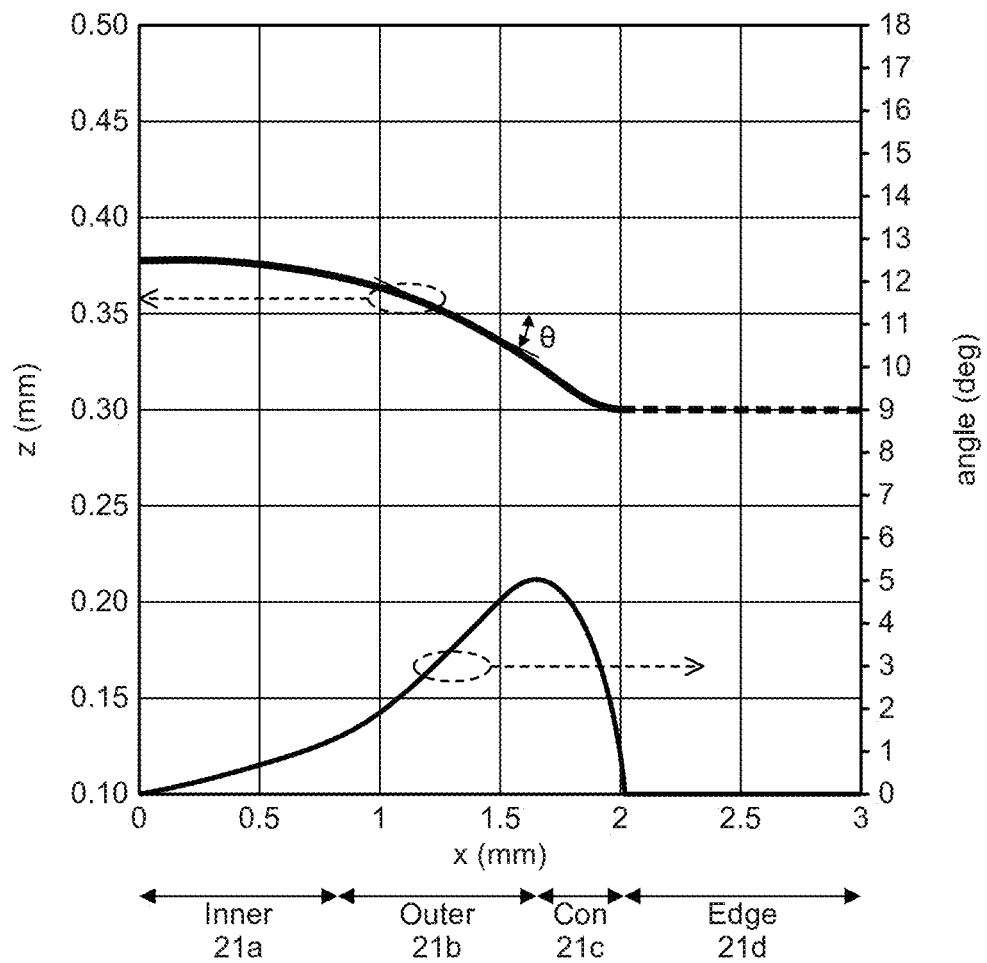

FIG. 8A and FIG. 8B illustrate an example of a shape of acoustic lens 21 according to the present embodiment. Incidentally, in FIGS. 8A and 8B, similar to FIGS. 4A, 4B, 5A, and 5B, the upper diagram (FIG. 8A) schematically illustrates the shape of acoustic lens 21, a graph of the lower diagram (FIG. 8B) illustrates the shape profile of the ultrasound radiation surface of acoustic lens 21 and the tangent angle profile of the ultrasound radiation surface of acoustic lens 21.

Figure 9:
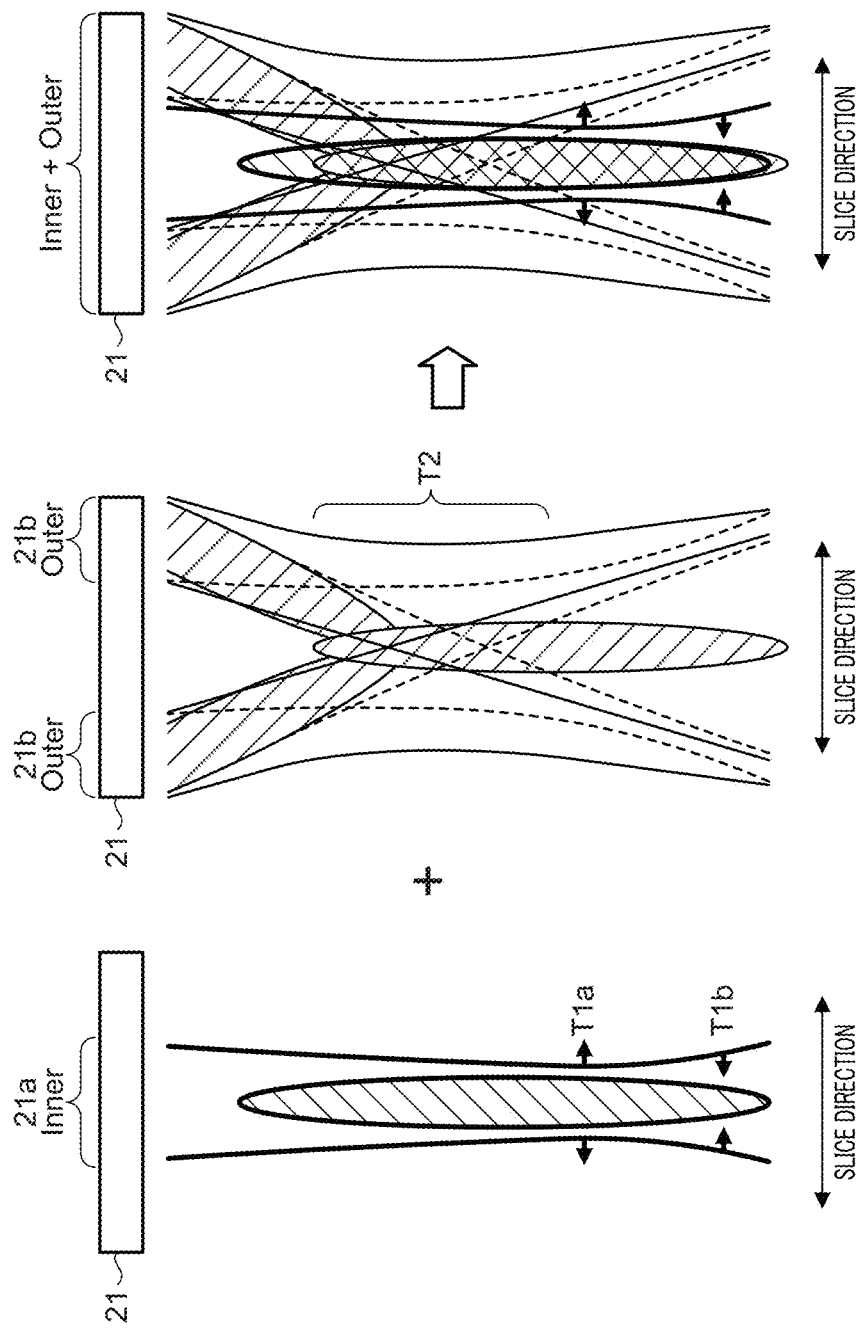
FIG. 9 describes a design concept of the acoustic lens according to the present embodiment.

FIG. 9 describes a design concept of acoustic lens 21 according to the present embodiment.

The lower diagram of FIG. 10 (FIG. 10B) illustrates a profile indicating a depth of a focal point (hereinafter may be referred to as a "focal depth") formed by a lens portion of each position within a surface of the ultrasound radiation surface of acoustic lens 21 according to the present embodiment (hereinafter may be abbreviated as a "focal depth profile"). In order to explain a difference between acoustic lens 21 according to the present embodiment and acoustic lenses 21 according to the related arts, FIGS. 10A and 10B illustrate a focal depth profile of acoustic lens 21X according to related art 1 (dotted line graph) and a focal depth profile of acoustic lens 21Y according to related art 2 (dash-dotted line graph) together with the focal depth profile of acoustic lens 21 according to the present embodiment (solid line graph).

Figure 10A:
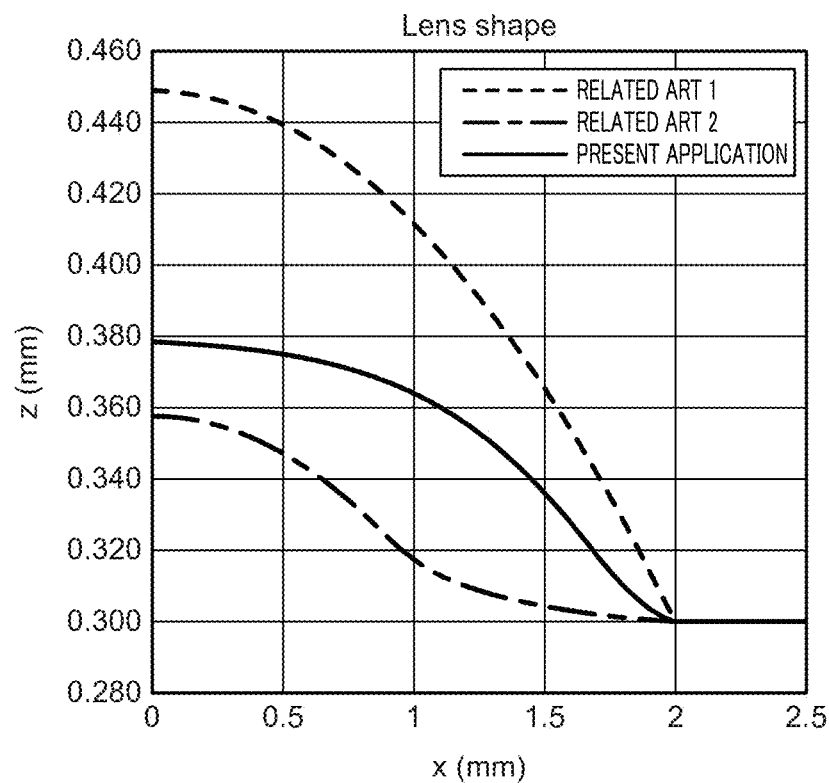
FIG. 10A and FIG. 10B illustrate a profile indicating a depth of a focal point formed by a lens portion of each position within a surface of an ultrasound radiation surface of the acoustic lens according to the present embodiment.
Figure 10B:
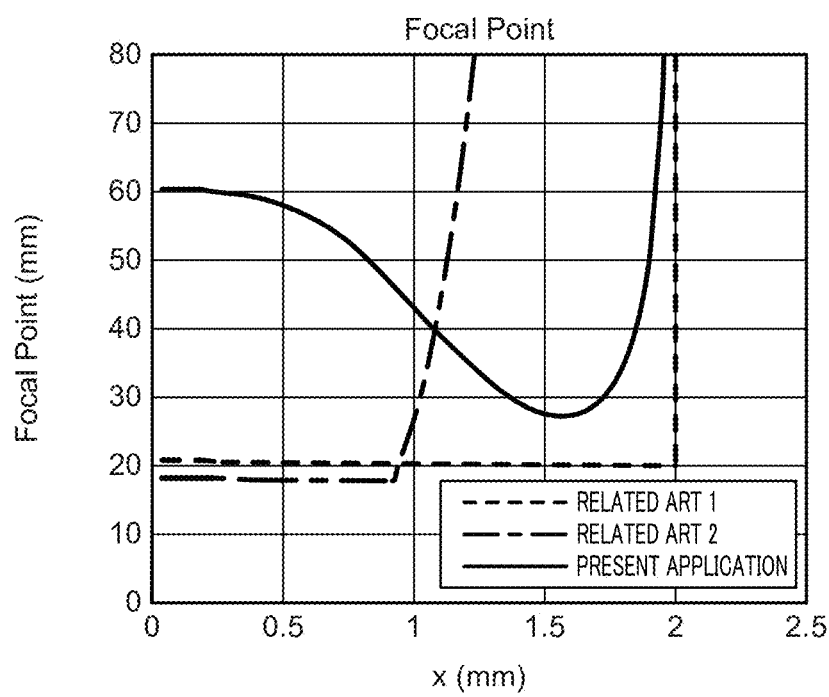

Note that, the above diagram of FIG. 10 (FIG. 10A) illustrates the shape profiles of the ultrasound radiation surfaces of acoustic lenses 21, 21X, and 21Y, the lower diagram of FIG. 10 (FIG. 10B) illustrates the focal depth profiles of acoustic lenses 21, 21X, and 21Y. A horizontal axis of the graph of FIG. 10B indicates positions of the ultrasound radiation surfaces of acoustic lenses 21, 21X, and 21Y in the slice direction with an x-coordinate system common to FIG. 10A, and a vertical axis of the graph of FIG. 10B indicates the focal depth formed by the lens portion at each of the positions. Incidentally, in any case of X=0 mm, a tangent of a lens surface becomes horizontal, and the focal depth at 0 mm is not illustrated because it becomes infinity.

Figure 11:
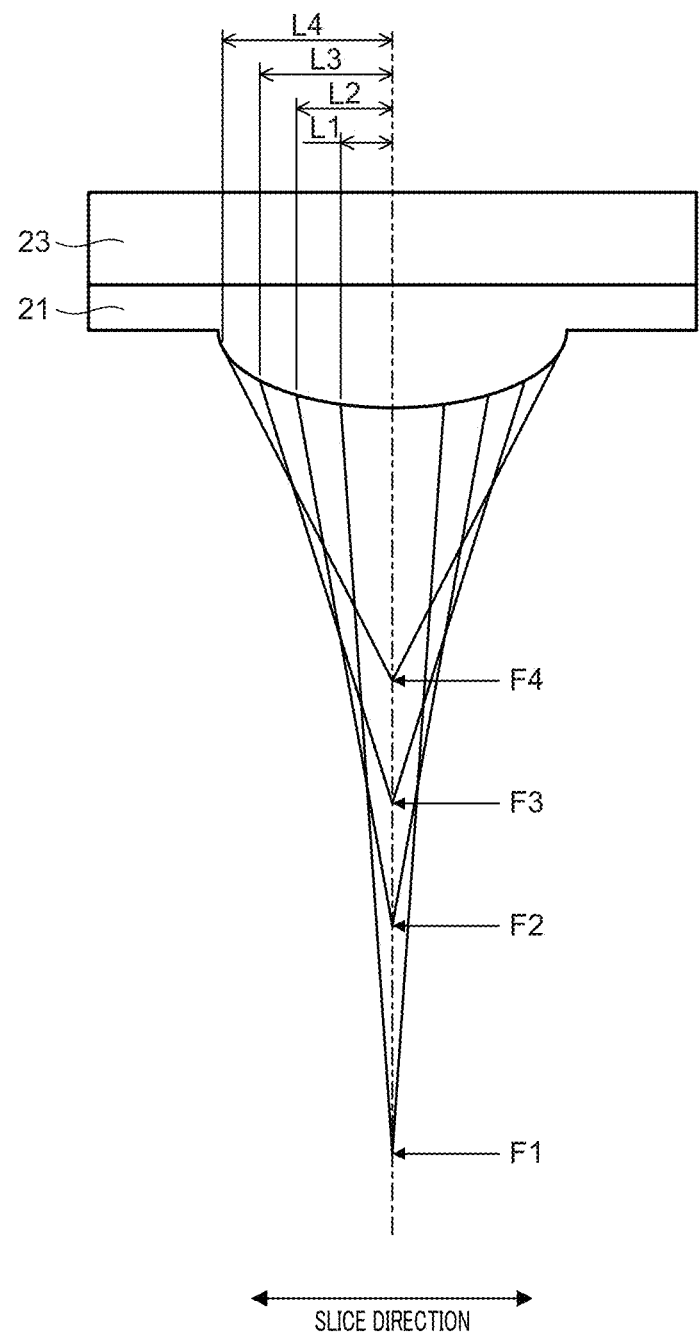
FIG. 11 schematically illustrates a focal depth profile of the acoustic lens according to the present embodiment by superimposing a shape profile.

FIG. 11 schematically illustrates a focal depth profile of acoustic lens 21 according to the present embodiment by superimposing on the shape profile of acoustic lens 21. F1, F2, F3, and F4, correspond, respectively, a focal point formed by the lens portion located in a position of distance of L1 from a lens center of acoustic lens 21, a f focal point formed by the lens portion located in a position of distance of L2 from a lens center of acoustic lens 21, a focal point formed by the lens portion located in a position of distance of L3 from a lens center of acoustic lens 21, and a focal point formed by the lens portion located in a position of distance of L4 from a lens center of acoustic lens 21.

Acoustic lens 21 according to the present embodiment includes, along the slice direction in its ultrasound radiation surface, inner area 21a located at the lens center portion and outer area 21b located at the lens outer side of inner area 21a adjacent to inner area 21a (see FIG. 8A). Acoustic lens 21 according to the present embodiment has a configuration in which inner area 21a forms a focal point at a position corresponding to the deep portion of the ultrasound beam (see an area with diagonal lines in the left diagram of FIG. 9) whereas outer area 21b forms a focal point at a position corresponding to the shallow portion of the ultrasound beam (see an area with diagonal lines in the central diagram of FIG. 9). That is, in acoustic lens 21 according to the present embodiment, the ultrasound radiated from inner area 21a supports the central axis sound pressure of the deep portion of the ultrasound beam, and the ultrasound radiated from outer area 21b supports the central axis sound pressure of the shallow portion of the ultrasound beam.

Incidentally, acoustic lens 21 according to the present embodiment, has an arch shape in which a center portion thereof in the slice direction protrudes (i.e., substantially semi-cylindrical shape), and has a linearly symmetrical shape with a center of the lens as a symmetrical axis. That is, outer area 21b is disposed, across inner area 21a along the slice direction, on both of one side and the other side of the lens outer side of inner area 21a, and is formed so as to focus on a shallower depth position than the focal depth of inner area 21a (see F2 in FIG. 11) on the lens central axis by outer area 21b of the one side and the other side of the lens outer side of inner area 21a.

Inner area 21a of acoustic lens 21 has, for example, a spherical shape, and outer area 21b of acoustic lens 21 has, for example, an aspherical shape in which the inclination of the tangent angle ($=d\theta/dx$) of each position within the surface of the ultrasound radiation surface gradually increases from a side of the lens center portion to the lens outer side (see FIGS. 8A and 8B). That is, outer area 21b of acoustic lens 21 has a shape in which the curvature of each position within the surface of the ultrasound radiation surface gradually increases from the side of the lens center portion to the lens outer side in a case where outer area 21b is set to the curved shape. Here, the phrase "gradually increasing" means monotonically and continuously increasing. Incidentally, as illustrated in FIGS. 8A and 8B, even in a connecting position between inner area 21a and outer area 21b of acoustic lens 21, the inclination of the tangent angle ($=d\theta/dx$) of the ultrasound radiation surface (i.e., curvature) gradually increases from the side of the lens center portion to the lens outer side without having a discontinuity.

In addition, in acoustic lens 21 illustrated in FIGS. 8A and 8B, the inclination of the tangent angle ($=d\theta/dx$) of each position within the surface of the ultrasound radiation surface of outer area 21b continuously changes in a non-fixed manner from an end of the side of the lens center portion to an end of the lens outer side (i.e., does not have a constant value).

In acoustic lens 21 according to the present embodiment, between outer area 21b and edge area 21d that is the outermost end of acoustic lens 21, connection area 21c is formed in which the inclination of the tangent angle ($=d\theta/dx$) of the ultrasound radiation surface gradually decreases from the side of the lens center portion to the lens outer side so as not to form an area where the curvature changes suddenly (see FIG. 8A). However, connection area 21c is, similar to edge area 21d, located at an end or outside of piezoelectric transducer 23a and has no significant impact on the beam properties of the ultrasound beam formed by acoustic lens 21. Thus, in other words, connection area 21c, similar to edge area 21d, may be omitted in constituting acoustic lens 21.

With such a shape, in acoustic lens 21 according to the present embodiment, the focal point formed by outer area 21b is at a position shallower than the focal point formed by inner area 21a. Moreover, in acoustic lens 21 according to the present embodiment, the focal depth formed by the lens portion of each position of inner area 21a and outer area 21b (i.e., focal depth profile) continuously becomes shallow from the side of the lens center portion to the lens outer side (see FIGS. 10B and 11).

Incidentally, in the focal depth profile according to the present embodiment illustrated in FIG. 10B, the focal depth is suddenly deepened at a position 1.5 mm or more away from a lens center to the lens outer side of the x-axis. This is because this area (area 1.5 mm or more away) corresponds to connection area 21c of a concave shape and edge area 21d of a flat shape.

With reference to FIG. 9, a design concept of acoustic lens 21 according to the present embodiment will be described in detail. As compared with acoustic lens 21Y according to related art 2, in acoustic lens 21 according to the present embodiment, the curvature as well as the size of opening of inner area 21a are reduced, and thereby a long focal point of inner area 21a is achieved (i.e., increasing the F-value). Consequently, a narrow portion of the ultrasound radiated from inner area 21a (T1a position in FIG. 9) (corresponding to a focal position of inner area 21a) is widened, and a deep portion of the ultrasound radiated from inner area 21a (T1b position in FIG. 9) (corresponding to a position deeper than the focal position of inner area 21a) is narrowed.

In addition, in acoustic lens 21 according to the present embodiment, the focal point formed by outer area 21b is set at a shallower position (T2 position in FIG. 9) than the focal point formed by inner area 21a, and the ultrasound radiated from outer area 21b supports the central axis sound pressure of the shallow portion of the ultrasound beam, the sound pressure being lowered by the long focal point of inner area 21a. Moreover, in acoustic lens 21 according to the present embodiment, the focal depth formed by the lens portion of each position of inner area 21a and outer area 21b draws a focal depth profile that becomes continuously shallow from the side of the lens center portion to the lens outer side.

With such a configuration, acoustic lens 21 according to the present embodiment achieves an ultrasound beam that is uniformly and thinly focused over a wide range from the shallow portion to the deep portion. In particular, in acoustic lens 21 according to the present embodiment, the end of outer area 21b on the lens outer side direction becomes the shallowest focal position, so that generation of the beam tails are suppressed in the shallow portion of the ultrasound beam. Thus, according to acoustic lens 21 according to the present embodiment, as compared with acoustic lens 21Y according to related art 2, it is possible to achieve an ultrasound beam that is uniformly and thinly focused over a wider range, and thereby expand the depth of field and suppress generation of the beam tails; as a result, the spatial resolution is improved.

Moreover, in acoustic lens 21 according to the present embodiment, a sound pressure peak of the central axis sound pressure can be reduced, which leads to a countermeasure to the Mechanical Index (MI) limit (output limit specified by considering an impact of ultrasound energy on a living body, and, in practical use, the MI value calculated based on the sound pressure peak of the central axis sound pressure or the like is required to be equal to or less than a predetermined value). That is, in acoustic lens 21 according to the present embodiment, it is possible to transmit a high-power ultrasound beam.

Next, with reference to FIGS. 12A to 12C and FIGS. 13A to 13C, an example of sound pressure distribution of the ultrasound beam formed using acoustic lens 21 according to the present embodiment and an example of an ultrasound image captured using acoustic lens 21 according to the present embodiment.

Figure 12C:
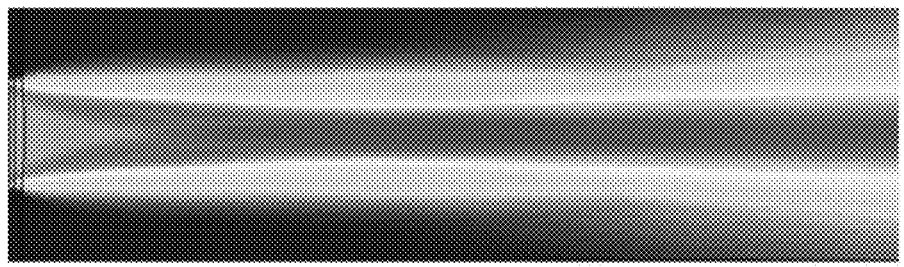
FIG. 12A, FIG. 12B, and FIG. 12C respectively illustrate sound pressure distribution of an ultrasound beam formed by the acoustic lens according to related art 1 (FIG. 12A), sound pressure distribution of an ultrasound beam formed by the acoustic lens according to related art 2 (FIG. 12B), and sound pressure distribution of an ultrasound beam formed by the acoustic lens according to the present embodiment (FIG. 12C)
Figure 12B:
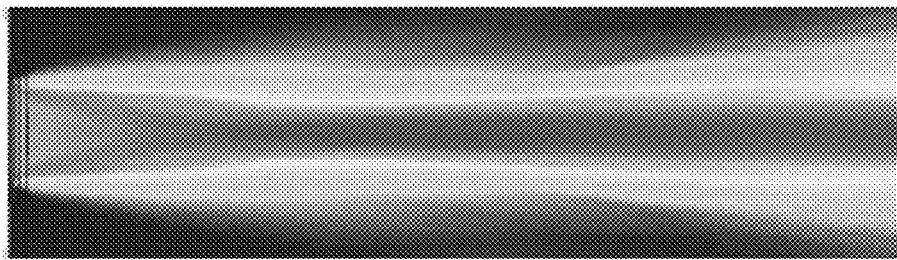
Figure 12A:
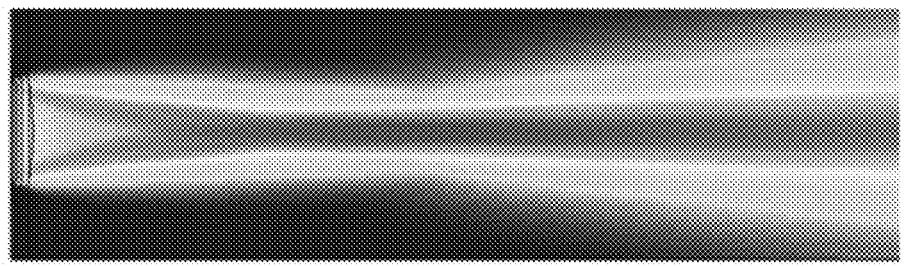

FIGS. 12A, 12B, and 12C respectively illustrate sound pressure distribution of an ultrasound beam formed by acoustic lens 21X according to related art 1 (FIG. 12A), sound pressure distribution of an ultrasound beam formed by acoustic lens 21Y according to related art 2 (FIG. 12B), and sound pressure distribution of an ultrasound beam formed by acoustic lens 21 according to the present embodiment (FIG. 12C). The sound pressure distribution of the ultrasound beams in FIGS. 12A, 12B, and 12C is calculated by simulation, and the simulation is conducted under the condition in which the configurations other than acoustic lens 21 are the same. In FIGS. 12A, 12B, and 12C, regions with the higher density indicate the higher sound pressure.

Figure 13C:
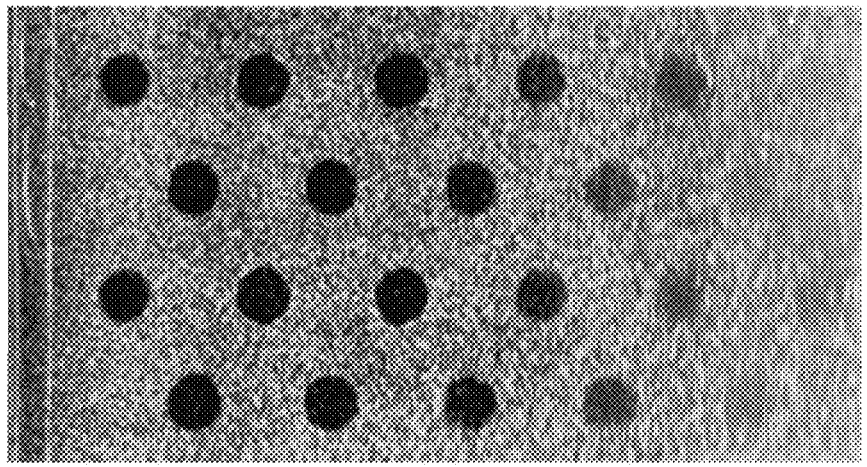
FIG. 13A, FIG. 13B, and FIG. 13C respectively illustrate an ultrasound image captured by using the acoustic lens according to related art 1 (FIG. 13A), an ultrasound image captured by using the acoustic lens according to related art 2 (FIG. 13B), and an ultrasound image captured by using the acoustic lens according to the present embodiment (FIG. 13C)
Figure 13B:
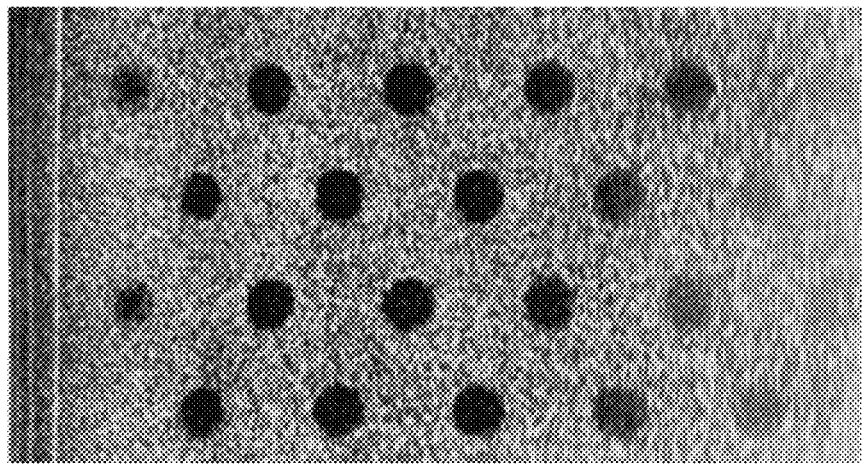
Figure 13A:
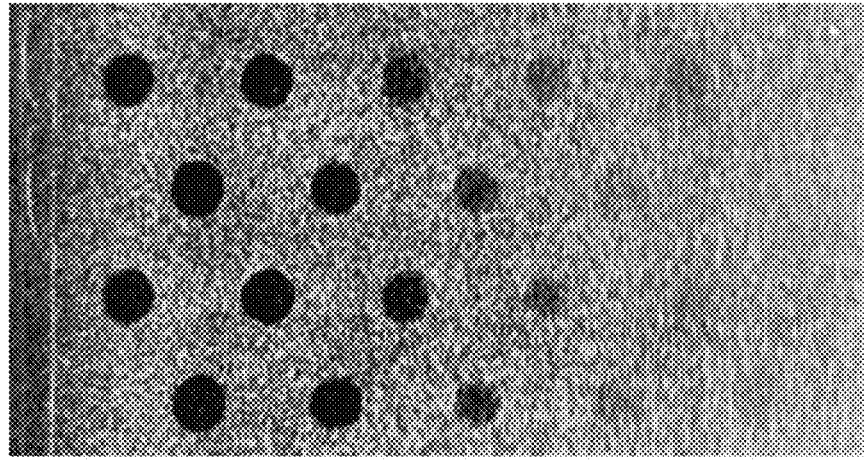

FIGS. 13A, 13B, and 13C respectively illustrate an ultrasound image captured by using acoustic lens 21X according to related art 1 (FIG. 13A), an ultrasound image captured by using acoustic lens 21Y according to related art 2 (FIG. 13B), and an ultrasound image captured by using acoustic lens 21 according to the present embodiment (FIG. 13C). Incidentally, each of the ultrasound images in FIGS. 13A, 13B, and 13C is an ultrasound image generated when a phantom for evaluating an ultrasound diagnostic apparatus (here, spherical cyst phantom: Gammex 408 LE).

From FIG. 12A, it is found that, in the sound pressure distribution of the ultrasound beam transmitted using acoustic lens 21 of related art 1, only the sound pressure at the depth position corresponding to the focal point of acoustic lens 21 is locally high and is narrowed, and a beam width at the deep portion of the ultrasound beam is diffused, and the sound pressure at a center is also lowered.

Moreover, from FIG. 12B, it is found that, in the sound pressure distribution of the ultrasound beam transmitted using acoustic lens 21 of related art 2, the sound pressure is uniformly and thinly focused over a certain range from the shallow portion to the deep portion of the ultrasound beam as compared with the sound pressure distribution of the ultrasound beam transmitted using acoustic lens 21 of related art 1. This is because acoustic lens 21 of related art 2 has a configuration in which the sound pressure at the shallow portion of the ultrasound beam is increased in inner area 21a, and the sound pressure at the deep portion of the ultrasound beam is increased in outer area 21b. However, in the sound pressure distribution of the ultrasound beam illustrated in FIG. 12B, it can be found that beam tails are generated and the beam width is widened because the ultrasound beam transmitted from outer area 21b partly diffuses outward and spreads in the shallow portion of the ultrasound beam.

Furthermore, from FIG. 12C, it is found that, in the sound pressure distribution of the ultrasound beam transmitted using acoustic lens 21 of the present embodiment, the sound pressure is uniformly and thinly focused over a wide range from the shallow portion to the deep portion of the ultrasound beam as compared with the sound pressure distribution of the ultrasound beam transmitted using acoustic lens 21 of related art 2. This is because, in the ultrasound beam transmitted using acoustic lens 21 according to the present embodiment, the beam tails that have been generated in the ultrasound beam transmitted using acoustic lens 21 of related art 2 are suppressed. In addition, it is also found from FIG. 12C that, in acoustic lens 21 according to the present embodiment, diffusion of the focal point formed by acoustic lens 21 toward the depth direction is more effectively performed, and, in the ultrasound beam transmitted using acoustic lens 21 according to the present embodiment, the central axis sound pressure of the ultrasound beam can be leveled from the shallow portion to the deep portion as compared with the ultrasound beam transmitted using acoustic lens 21 of related art 2.

Meanwhile, as can be seen by comparison between FIG. 13A and FIG. 13B, an ultrasound image captured using acoustic lens 21Y according to related art 2 is clear in the deep portion as compared with an ultrasound image captured using acoustic lens 21X according to related art 1. On the other hand, the ultrasound image captured using acoustic lens 21Y according to related art 2 is a blurred in the shallow portion as compared with the ultrasound image captured using acoustic lens 21X according to related art 1.

In this respect, as can be seen by comparing FIG. 13C with FIG. 13A and FIG. 13B, an ultrasound image captured using acoustic lens 21 according to the present embodiment is clear in both shallow and deep portions. That is, using acoustic lens 21 according to the present embodiment allows expansion of the depth of field and improvement of the spatial resolution than when using acoustic lenses 21X and 21Y according to, respectively, related art 1 and related art 2.

Here, a description will be given of a more preferable embodiment of acoustic lens 21 according to the present embodiment.

The shape of acoustic lens 21 according to the present embodiment can be defined by, for example, the minimum F-value, the F-value ratio, the focal depth profile, and the shape of connection area 21c.

Here, the "minimum F value" is a value defined by the minimum value among the F values at respective positions of acoustic lens 21. For example, when a distance from the lens center=1.8 mm and a focal distance at the position=18.4 mm, the minimum F value at the position=18.4/(1.8*2)=5.1, and the minimum F value will be 5.1 in a case where this F value is the minimum in all positions. Furthermore, the "F value ratio" is a value defined by the value obtained by dividing the F value near the center of the lens of the acoustic lens by the minimum F value (the near center conversion F value/minimum F value) (provided that, the near center conversion F value is an F value obtained from the near center focal distance and the width of the entire ultrasound radiation surface).

The minimum F value of acoustic lens 21 is preferably from 5 to 7. When the minimum F value is smaller than 5, a depiction of the shallow portion is improved, but an inclination angle of the ultrasound beam radiated from the lens portion (piezoelectric transducer 23a) at the position corresponding to the minimum F value increases, resulting in higher sound pressure in the shallow portion and an increase in the MI value. In addition, a deep depiction is lowered because the ultrasound beam expands in a portion deeper than or at the focal point. On the other hand, when the minimum F value is larger than 7, a diffusion impact becomes larger than that with the focusing by the ultrasound beam, which also lowers the deep depiction.

The F value ratio of acoustic lens 21 is preferably within the range of 2.5 to 3.5 when the minimum F value is within the range of 5 to 7. When the F value ratio is smaller than 2.5, a change in the focal point in the lens becomes smaller, and a focal range of the ultrasound beam is narrowed, and thus, an increase in the MI value due to the sound pressure concentration is caused, resulting in that a transmission voltage tends to be regulated. On the other hand, when the F value ratio becomes larger than 3.5, the focusing properties of the ultrasound beam radiated from the vicinity of a center become insufficient, and the ultrasound beam expands by diffusion in the deep portion, which lowers the deep depiction.

The focal depth profiles of inner area 21a and outer area 21b of acoustic lens 21 preferably continuously vary, without discontinuous part, from a center of the lens of inner area 21a to an end of outer area 21b on the lens outer side. Eliminating the discontinuous part reliably prevents a valley-shaped portion in which bubbles in the ultrasound jelly easily accumulate from being formed in an outer shape of acoustic lens 21, and thus it is possible to suppress deterioration of image quality caused by bubbles in the ultrasound jelly. Here, the state of no discontinuous part means a state in which, in the focal depth profile (see FIG. 10B), the amount of variation of the focal depth per 0.1 mm in the x-axis plus direction is 10 mm or more. Incidentally, in acoustic lens 21 according to the present embodiment, the valley-shaped portion is possibly formed in connection area 21c, but as described above, since connection area 21c is located at the end or outside of piezoelectric transducer 23a and has no significant impact on the beam properties of the ultrasound beam formed by acoustic lens 21; thus, formation of the valley-shaped portion in this area does not cause a problem.

Moreover, the focal depth profile of outer area 21b of acoustic lens 21 preferably varies continuously in a non-fixed manner from an end of outer area 21b on the side of the lens center portion to an end of outer area 21b on the lens outer side. This makes it possible to form a more uniformly and thinly focused ultrasound beam over a wide range from the shallow portion to deep portion and to reduce the sound pressure peak of the central axis sound pressure. Here, the state of varying continuously in a non-fixed manner means a state in which, in the focal depth profile (see FIG. 10B), the amount of variation of the focal depth per 0.1 mm in the x-axis plus direction is less than 1 mm.

The shape of connection area 21c of acoustic lens 21 is not particularly limited and may have various shapes such as a concave curve line, a convex curve line, a straight line, but it is preferably the straight line shape in a case where a lens is to be provided in a manufacturing process for attaching the lens to the transducer which has been manufactured in advance. The manufacturing process of attaching the lens requires to produce a lens shape larger considering that the attachment is displaced to some extent. Connection area 21c having a straight line makes it easier to ensure a lens width for covering the displacement by the straight line shape being stretched as required. However, this does not apply to the case of the manufacturing process for performing shape processing after attaching the lens member.

EXAMPLES

Next, with reference to FIGS. 14A and 14B to FIGS. 20A and 20B, a description will be given of various shapes of acoustic lens 21 configured based on the design concept of acoustic lens 21 according to the present application.

Figure 14A:
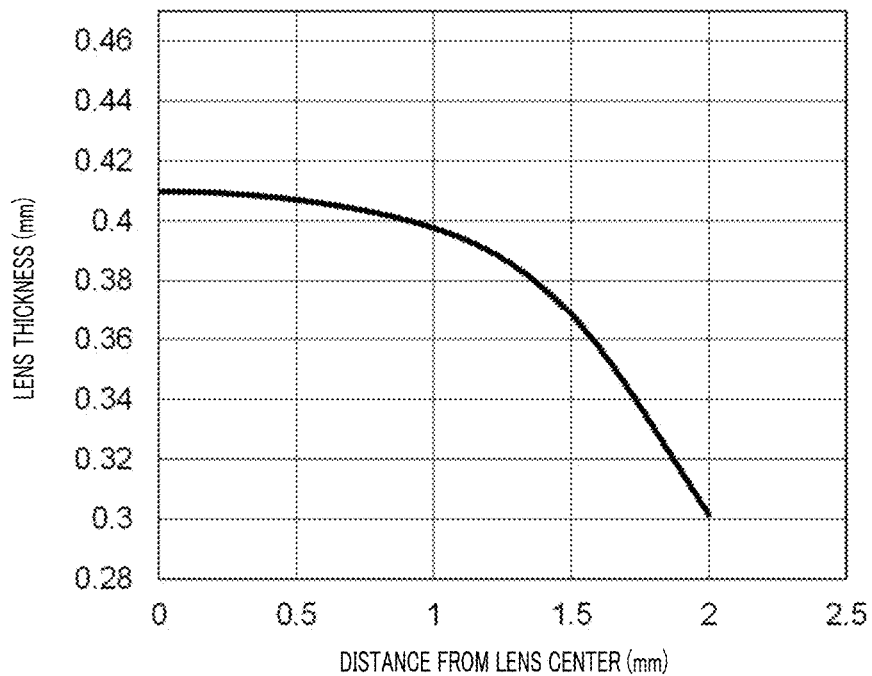
FIG. 14A and FIG. 14B illustrate a shape of an acoustic lens according to Example 1.
Figure 14B:
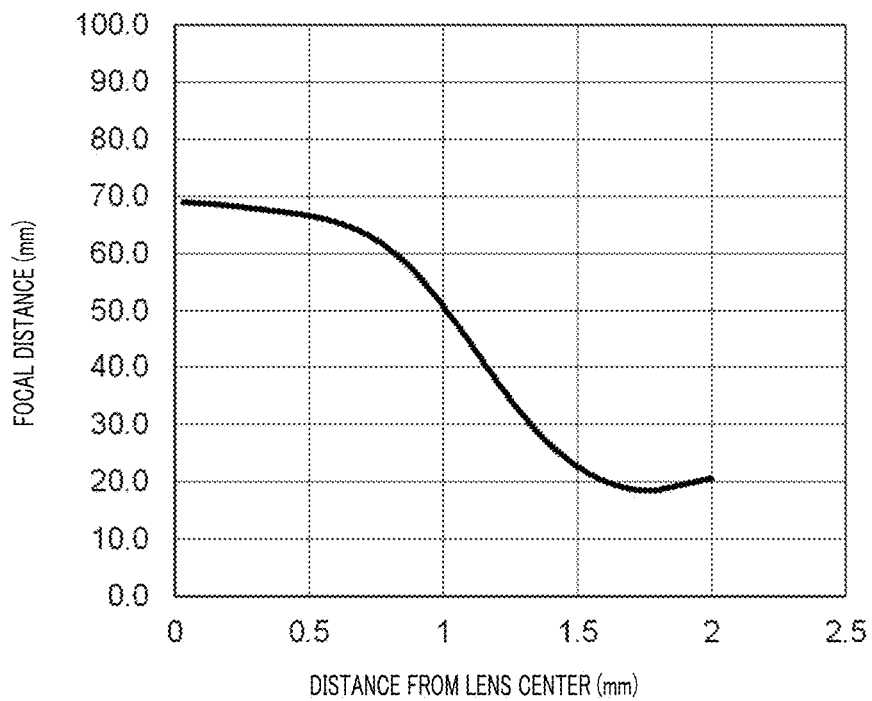

FIG. 14A illustrates a shape profile of acoustic lens 21 according to Example 1, and FIG. 14B illustrates a focal depth profile of acoustic lens 21 according to Example 1. Acoustic lens 21 according to Example 1 is acoustic lens 21 manufactured by setting the near center focal distance (mm) to 69.0 mm, the near center conversion F value to 17.2, the shortest focal distance (mm) to 18.4 mm, the minimum F value to 5.1, and the F value ratio to 3.4, based on the design concept of acoustic lens 21 according to the present application.

Figure 15A:
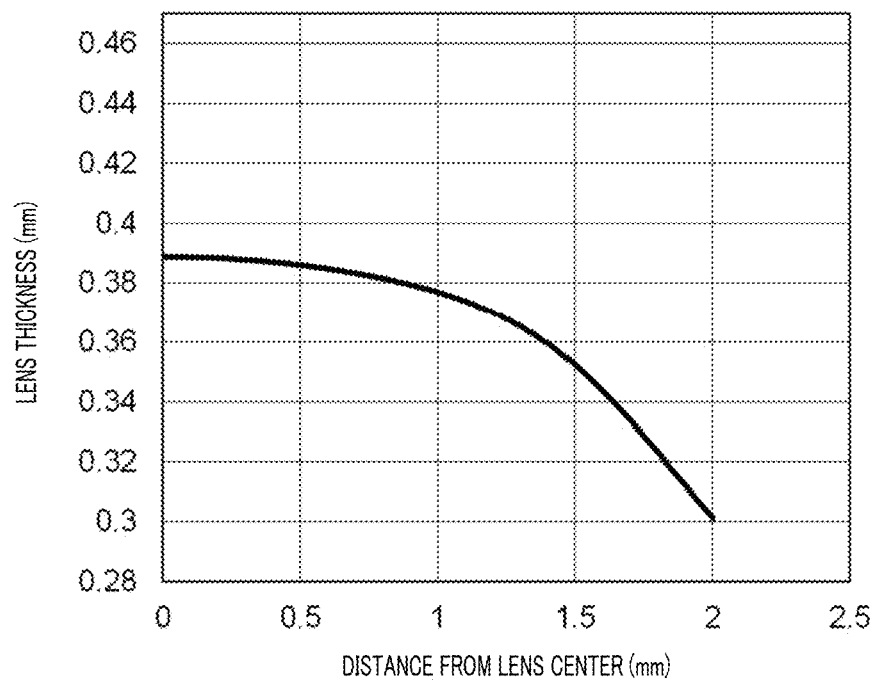
FIG. 15A and FIG. 15B illustrate a shape of an acoustic lens according to Example 2.
Figure 15B:
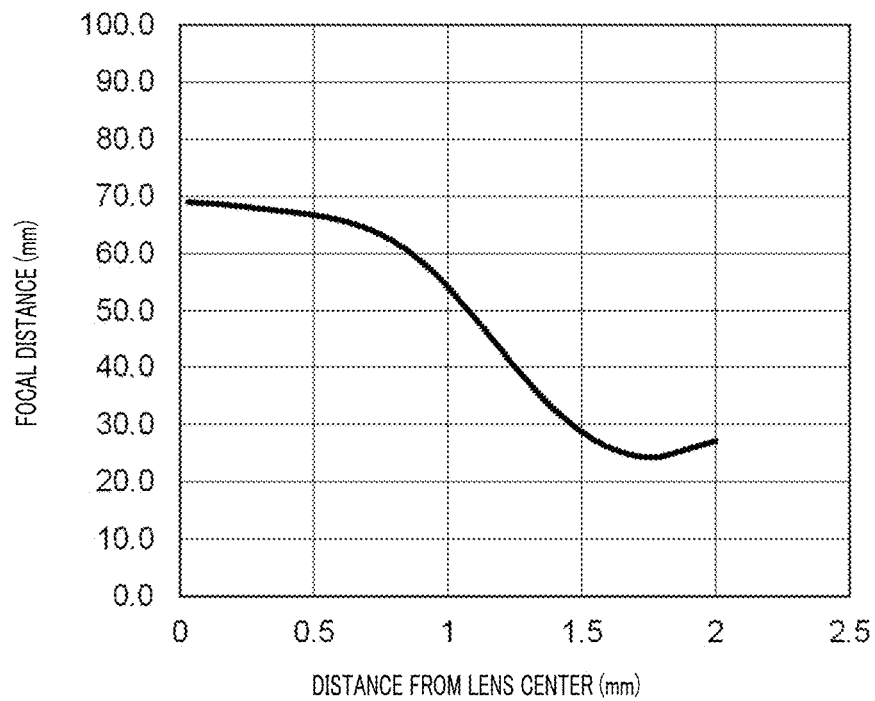

FIG. 15A illustrates a shape profile of acoustic lens 21 according to Example 2, and FIG. 15B illustrates a focal depth profile of acoustic lens 21 according to Example 2. Acoustic lens 21 according to Example 2 is acoustic lens 21 manufactured by setting the near center focal distance (mm) to 69.0 mm, the near center conversion F value to 17.2, the shortest focal distance (mm) to 18.4 mm, the minimum F value to 5.1, and the F value ratio to 3.4, based on the design concept of acoustic lens 21 according to the present application.

Figure 16A:
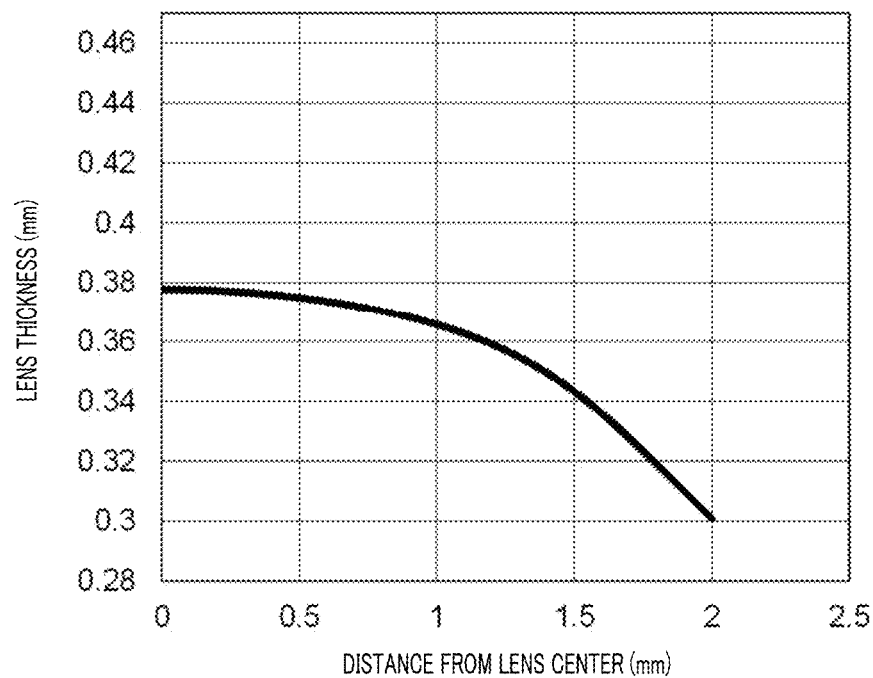
FIG. 16A and FIG. 16B illustrate a shape of an acoustic lens according to Example 3.
Figure 16B:
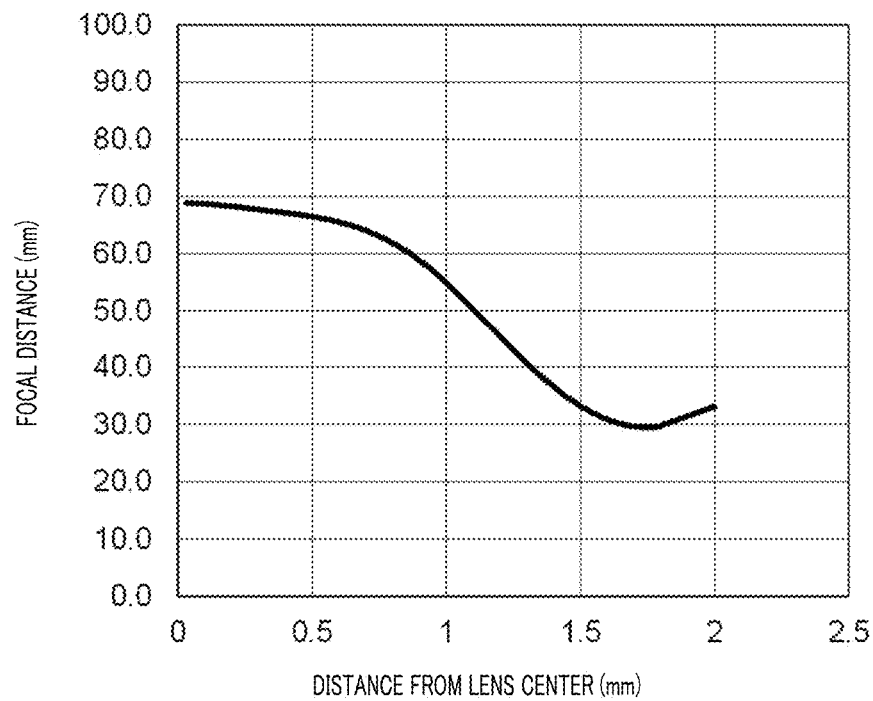

FIG. 16A illustrates a shape profile of acoustic lens 21 according to Example 3, and FIG. 16B illustrates a focal depth profile of acoustic lens 21 according to Example 3. Acoustic lens 21 according to Example 3 is acoustic lens 21 manufactured by setting the near center focal distance (mm) to 69.0 mm, the near center conversion F value to 17.2, the shortest focal distance (mm) to 29.5 mm, the minimum F value to 8.3, and the F value ratio to 2.1, based on the design concept of acoustic lens 21 according to the present application.

Figure 17A:
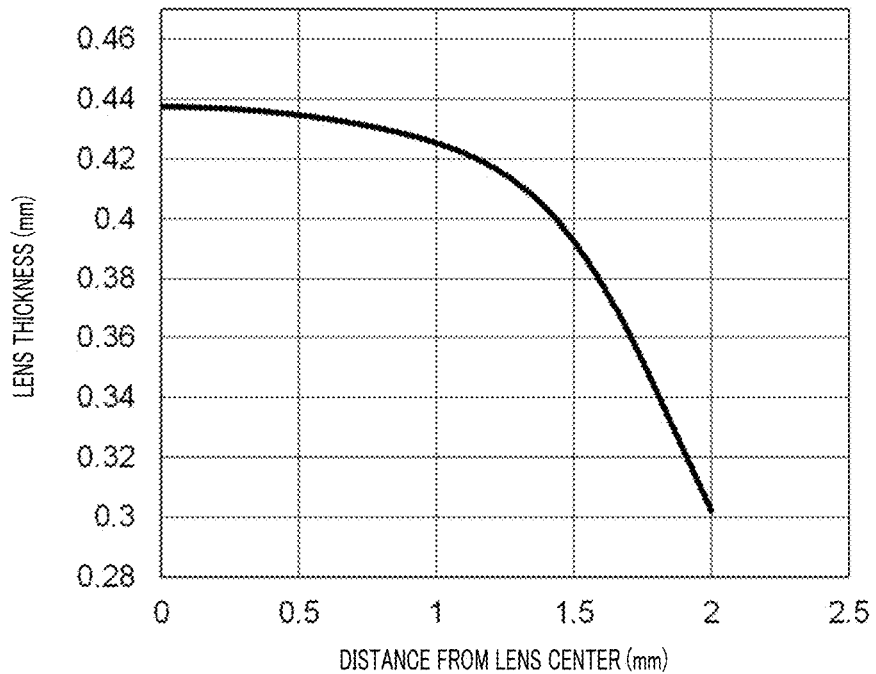
FIG. 17A and FIG. 17B illustrate a shape of an acoustic lens according to Example 4.
Figure 17B:
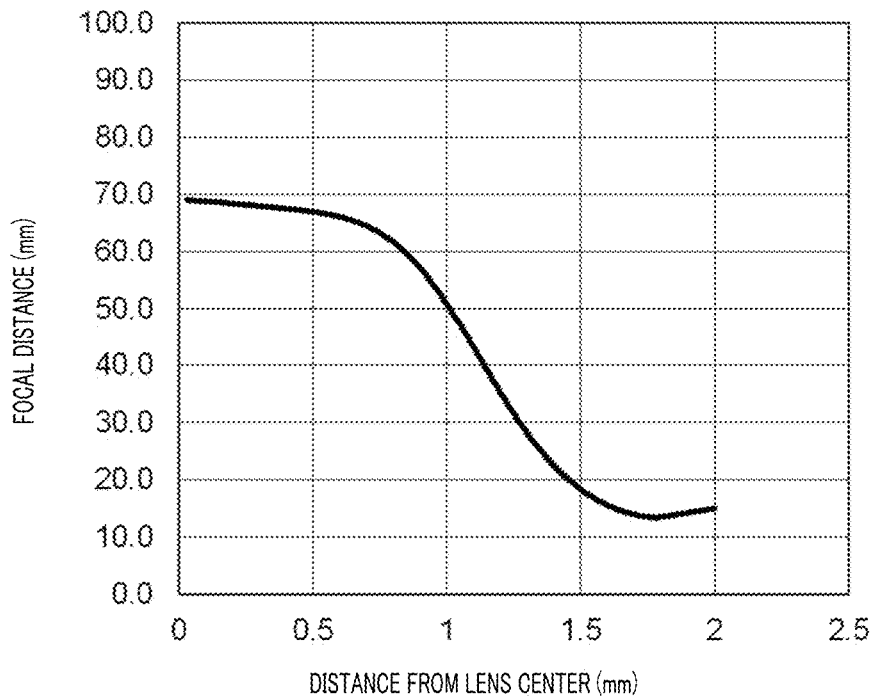

FIG. 17A illustrates a shape profile of acoustic lens 21 according to Example 4, and FIG. 17B illustrates a focal depth profile of acoustic lens 21 according to Example 4. Acoustic lens 21 according to Example 4 is acoustic lens 21 manufactured by setting the near center focal distance (mm) to 69.0 mm, the near center conversion F value to 17.2, the shortest focal distance (mm) to 13.4 mm, the minimum F value to 3.7, and the F value ratio to 4.6, based on the design concept of acoustic lens 21 according to the present application.

Figure 18A:
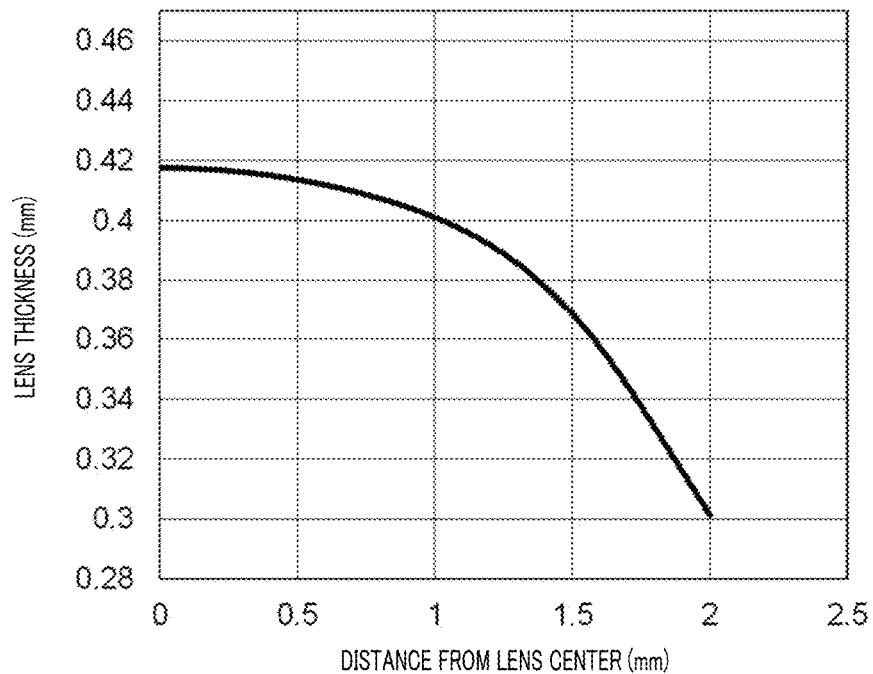
FIG. 18A and FIG. 18B illustrate a shape of an acoustic lens according to Example 5.
Figure 18B:
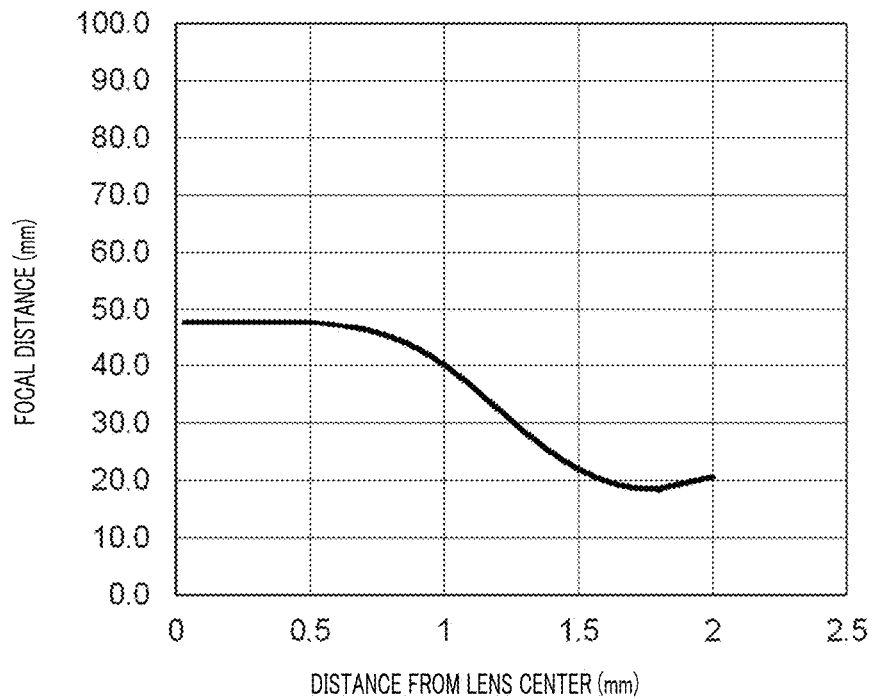

FIG. 18A illustrates a shape profile of acoustic lens 21 according to Example 5, and FIG. 18B illustrates a focal depth profile of acoustic lens 21 according to Example 5. Acoustic lens 21 according to Example 5 is acoustic lens 21 manufactured by setting the near center focal distance (mm) to 47.7 mm, the near center conversion F value to 11.9, the shortest focal distance (mm) to 18.4 mm, the minimum F value to 5.1, and the F value ratio to 2.3, based on the design concept of acoustic lens 21 according to the present application.

Figure 19A:
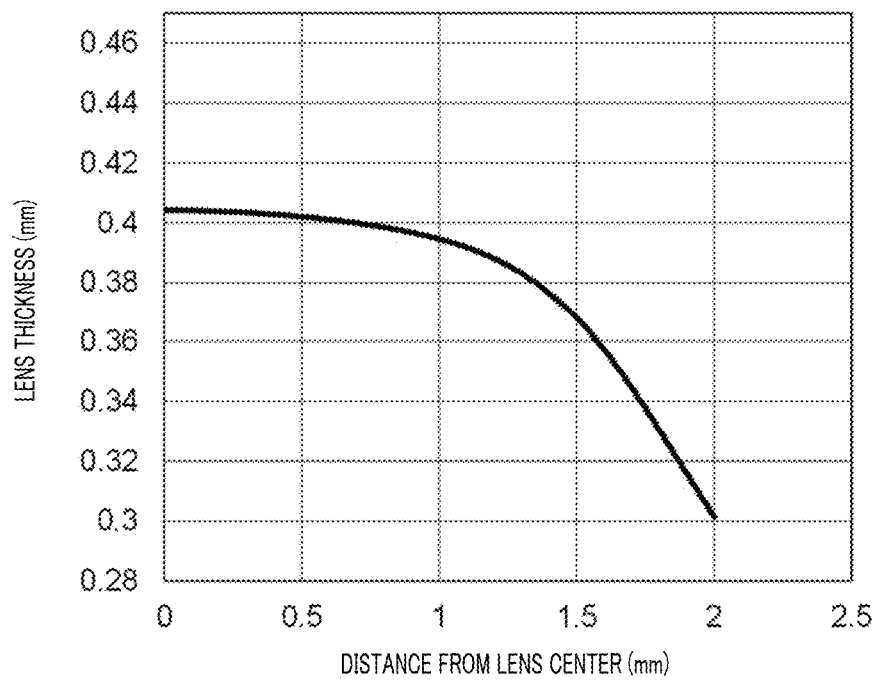
FIG. 19A and FIG. 19B illustrate a shape of an acoustic lens according to Example 6.
Figure 19B:
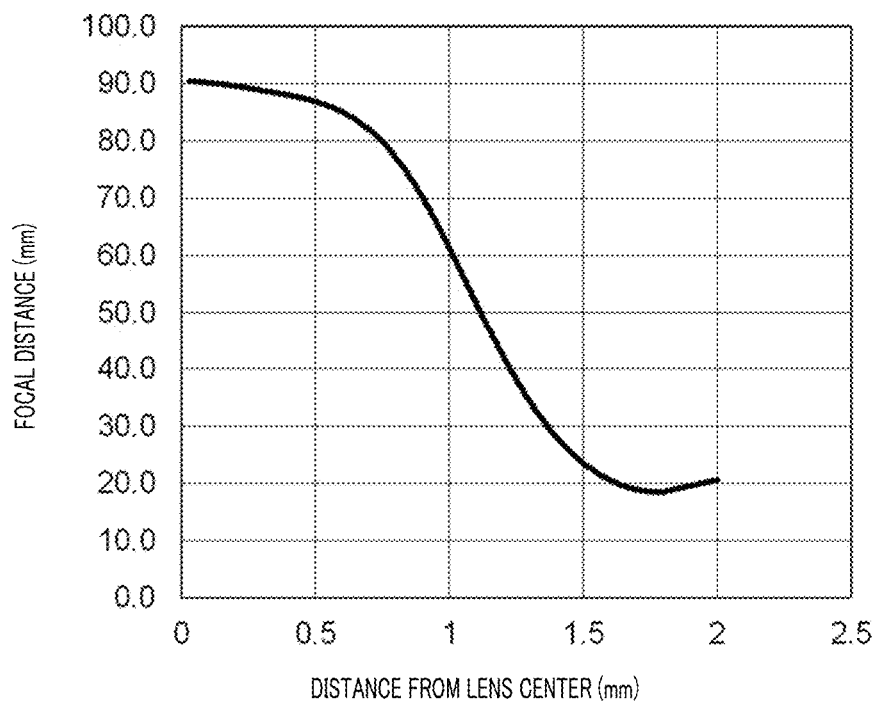

FIG. 19A illustrates a shape profile of acoustic lens 21 according to Example 6, and FIG. 19B illustrates a focal depth profile of acoustic lens 21 according to Example 6. Acoustic lens 21 according to Example 6 is acoustic lens 21 manufactured by setting the near center focal distance (mm) to 90.5 mm, the near center conversion F value to 22.6, the shortest focal distance (mm) to 18.4 mm, the minimum F value to 5.1, and the F value ratio to 4.4, based on the design concept of acoustic lens 21 according to the present application.

Figure 20A:
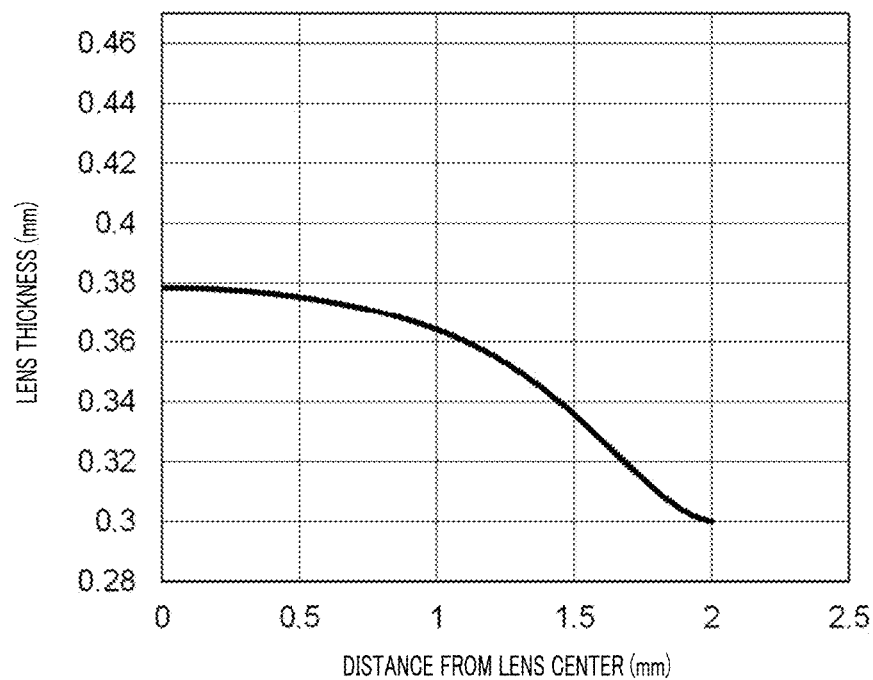
FIG. 20A and FIG. 20B illustrate a shape of an acoustic lens according to Example 7.
Figure 20B:
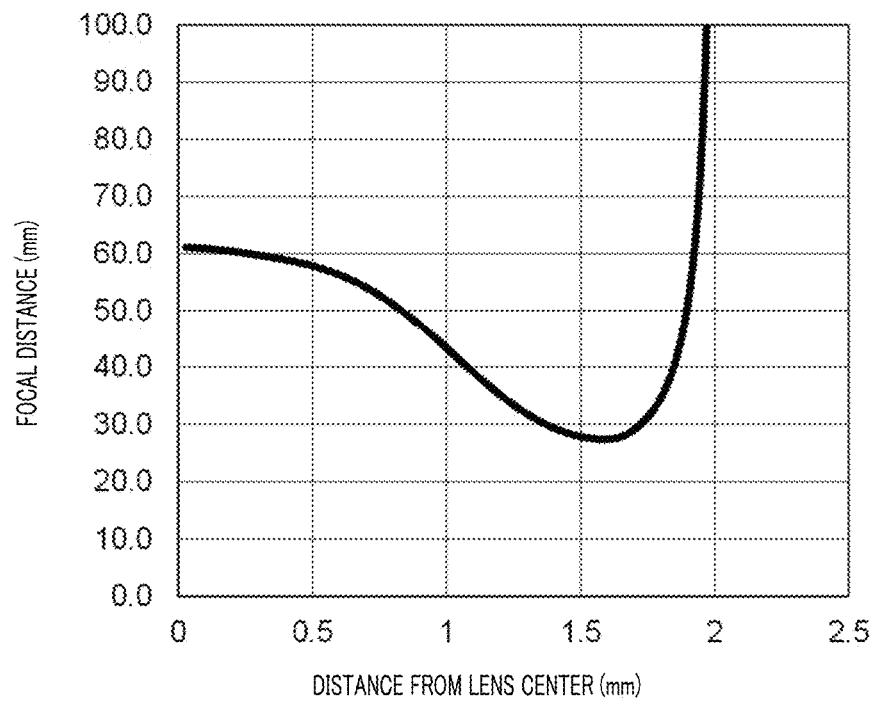

FIG. 20A illustrates a shape profile of acoustic lens 21 according to Example 7, and FIG. 20B illustrates a focal depth profile of acoustic lens 21 according to Example 7. Acoustic lens 21 according to Example 7 is acoustic lens 21 manufactured by setting the near center focal distance (mm) to 61.2 mm, the near center conversion F value to 15.3, the shortest focal distance (mm) to 27.4 mm, the minimum F value to 8.4, and the F value ratio to 1.8, based on the design concept of acoustic lens 21 according to the present application.

In acoustic lens 21 (FIGS. 14A and 14B to FIGS. 19A and 19B) according to Examples 1 to 6, connection area 21c has a linear shape, whereas in acoustic lens 21 (FIGS. 20A and 20B) according to Example 7, connection area 21c has a concave shape.

Verification Experiment

Next, an experimental result of a verification experiment conducted to evaluate performance of acoustic lens 21 according to the present application is indicated. Note that, this verification experiment has been conducted, using a Gammex 408 LE spherical cyst phantom.

FIG. 21 illustrates results of performance evaluations of acoustic lens 21 according to the present application, acoustic lens 21X according to related art 1, and acoustic lens 21Y according to related art 2 from the three perspectives of "Clutter Energy to Total Energy Ratio (CTR) (db)," "Penetration (cm)," and "accumulation of Gel air bubbles."

Figure 22A:
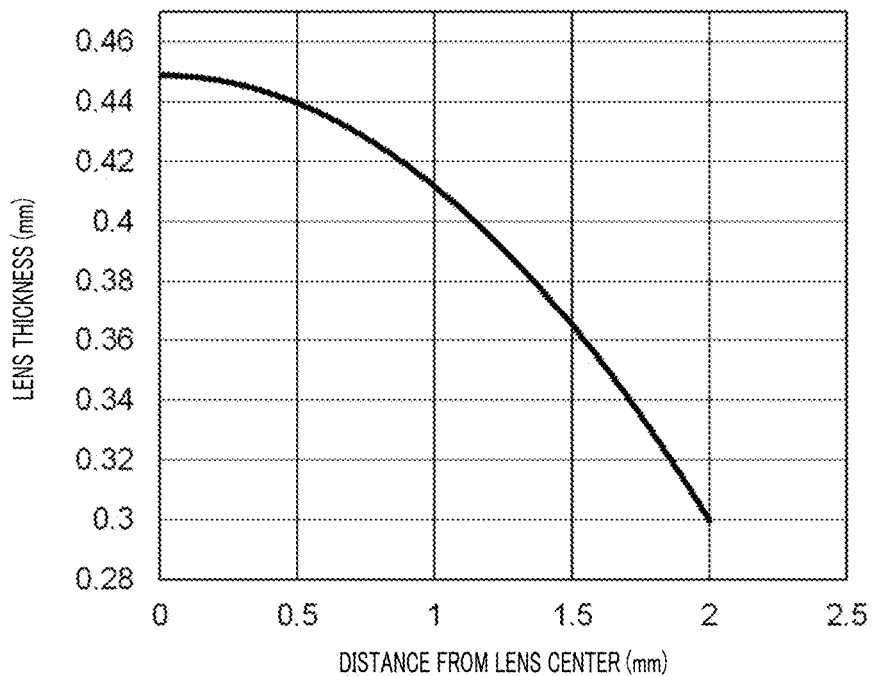
FIG. 22A and FIG. 22B illustrate a shape of an acoustic lens according to Comparative Example 1.
Figure 22B:
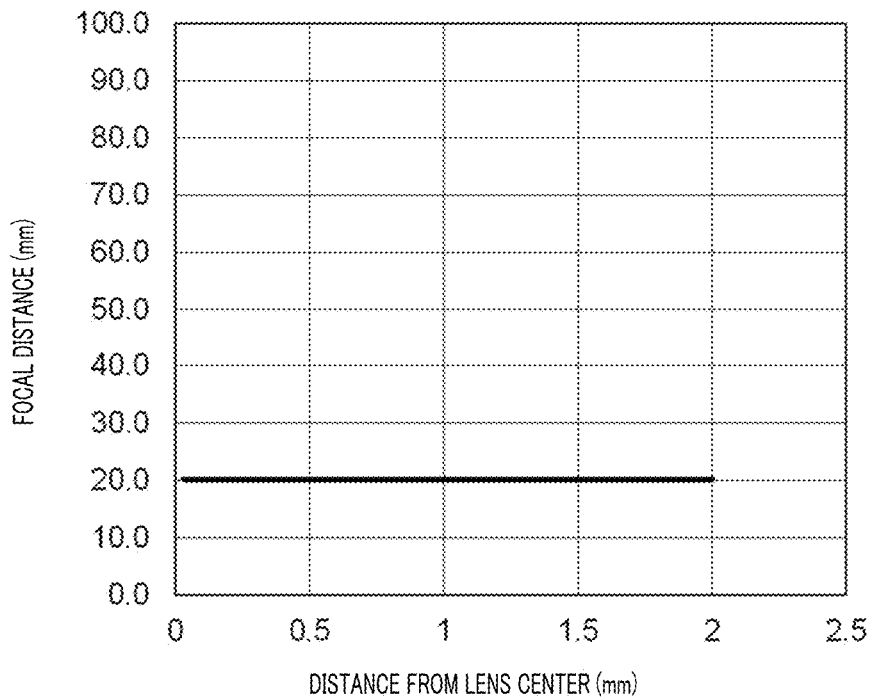
Figure 23A:
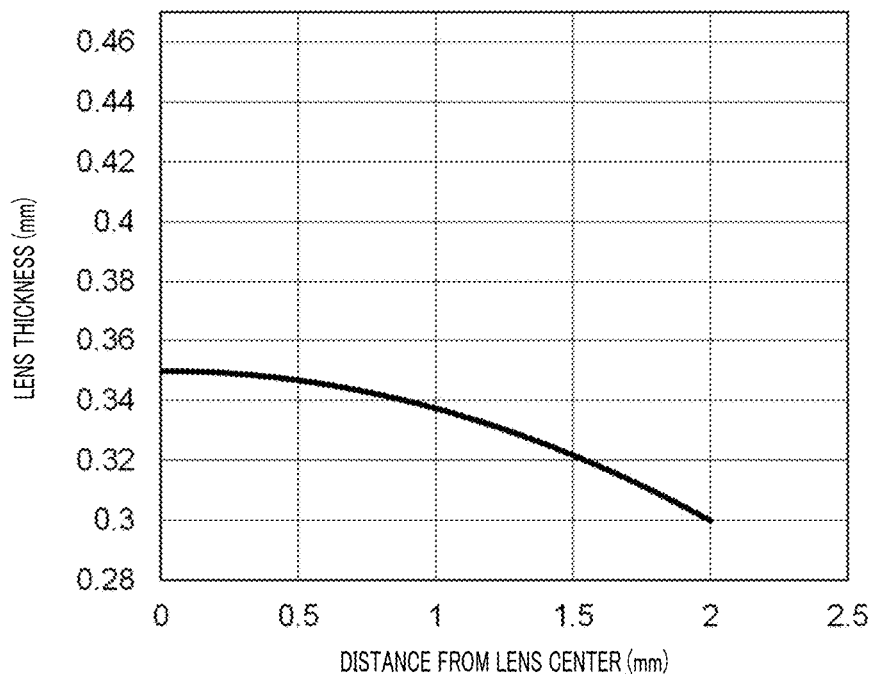
FIG. 23A and FIG. 23B illustrate a shape of an acoustic lens according to Comparative Example 2.
Figure 23B:
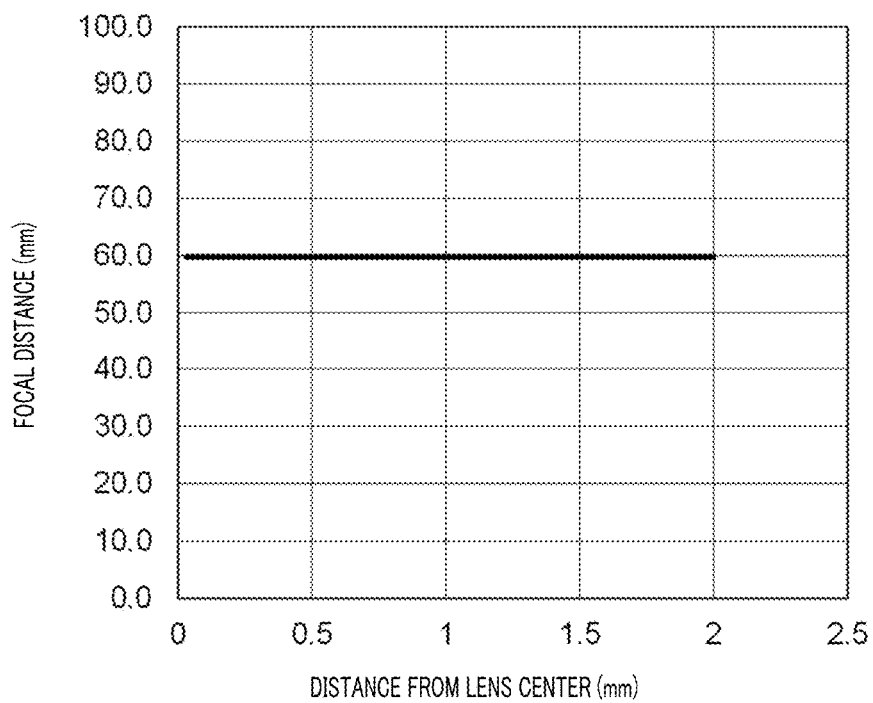
Figure 24A:
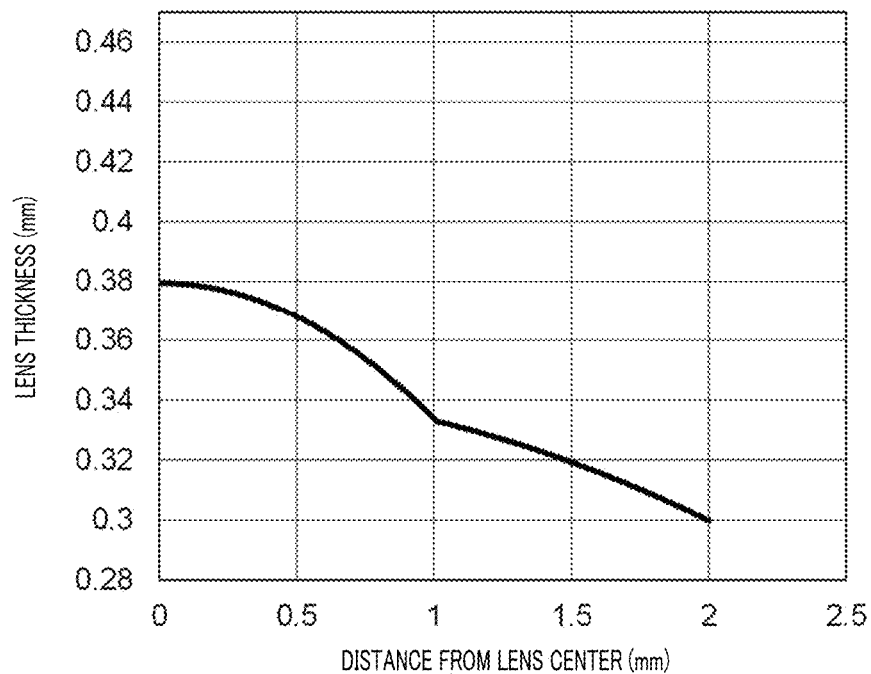
FIG. 24A and FIG. 24B illustrate a shape of an acoustic lens according to Comparative Example 3.
Figure 24B:
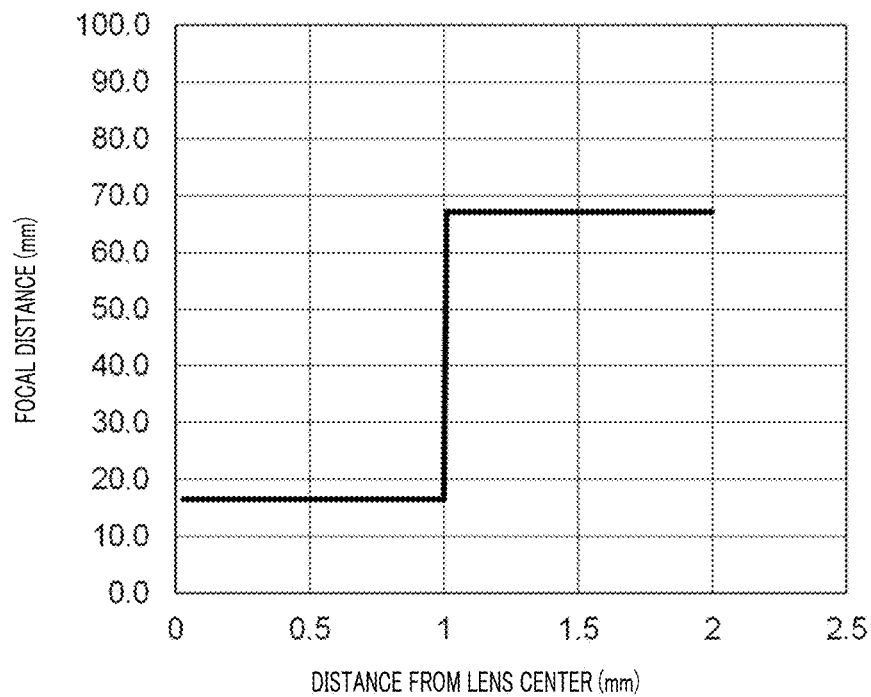
Figure 25A:
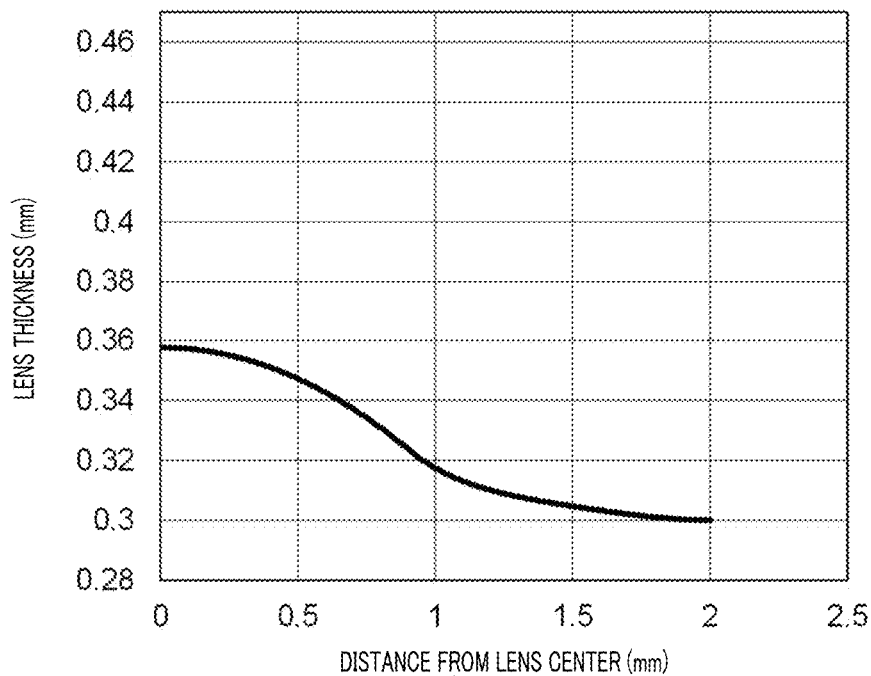
FIG. 25A and FIG. 25B illustrate a shape of an acoustic lens according to Comparative Example 4.
Figure 25B:
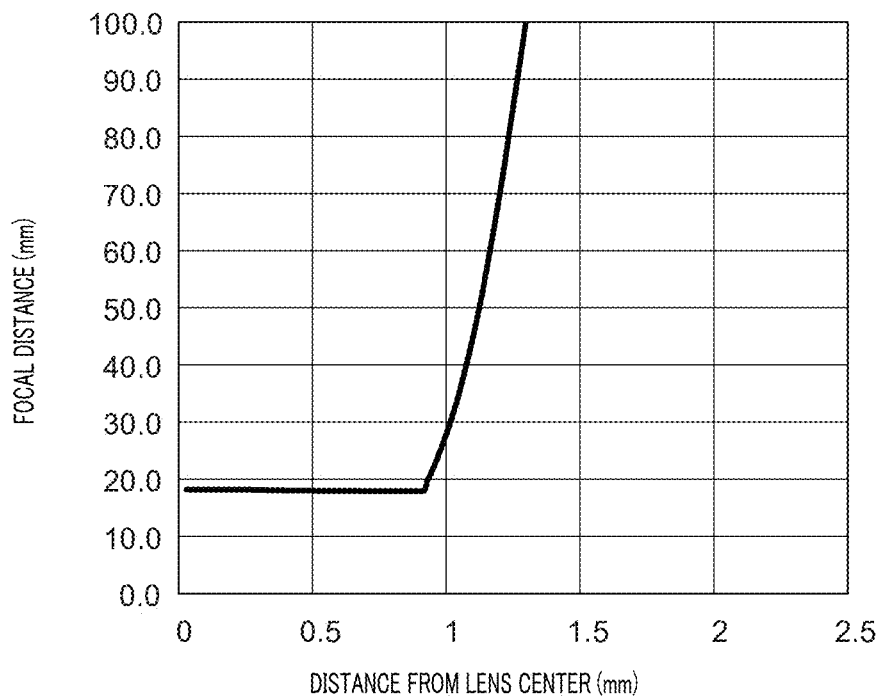

Here, as acoustic lens 21 according to the present application, an acoustic lens according to Example 2 illustrated in FIGS. 15A and 15B was used. Moreover, as acoustic lens 21X according to related art 1, an acoustic lens according to Comparative Example 1 illustrated in FIGS. 22A and 22B and an acoustic lens according to Comparative Example 2 illustrated in FIGS. 23A and 23B were used. Furthermore, as acoustic lens 21Y according to related art 2, an acoustic lens according to Comparative Example 3 illustrated in FIGS. 24A and 24B and an acoustic lens according to Comparative Example 4 illustrated in FIGS. 25A and 25B were used. Design parameters of the acoustic lens according to the present application and the acoustic lenses according to Comparative Examples 1 to 4 are described in FIG. 21.

"CTR" is a depiction index of an echoless part and serves as an index which indicates a depth of field and spatial resolution of each depth position. CTR can be calculated with the following equation in the image of 256 tones. Note that, the larger the CTR value (dB) is, the better the depiction of the echoless portion is. On the other hand, when luminance of the entire echoless part is increased or when the apparent size of the echoless part is reduced by a boundary protruding to the echoless part, the CTR value decreases.

$$CTR[\text{dB}] = (L_{background} - L_{cyst}) \times \frac{DR}{255} \quad \text{Equation}$$

where:
$L_{background}$=mean luminance value of phantom background area (not echoless area)
$L_{cyst}$32 mean luminance value of phantom echoless area measured in its original size (in this time, image area corresponding to 4 mmΦ)
DR=Dynamic range (dB)

"Penetration (cm)" is an index of the depth of field. Here, an evaluation value of the Penetration is set to a depth that makes correlation coefficients of two images equal to 0.5 or more when the two images are captured at the same point of Gammex 408 LE sphere cyst phantom under a situation where no echoless target is present and all background parts are to be depicted.

"Accumulation of Gel air bubbles" is an evaluation item related to the presence or absence of an image defect under a situation where bubbles are contained in an ultrasound jelly with a bubbler and, using this jelly, the Gammex 408 LE spherical cyst phantom was observed. Here, in addition to the case where accumulation of Gel air bubbles has not occurred, even the case where the image defect due to bubbles could have been eliminated by an operation of pressing the acoustic lens against the cyst phantom alone was evaluated as the accumulation of Gel air bubbles is "absent."

As can be seen from FIG. 21, the acoustic lens according to the present application has the CTR value higher than that of the acoustic lenses according to Comparative Examples 1 to 4 from the shallow portion to the deep portion. In addition, the acoustic lens according to the present application has the Penetration (cm) higher than that of the acoustic lenses according to Comparative Examples 1 to 4. Moreover, the accumulation of Gel air bubbles was not generated in the acoustic lens according to the present application, although the accumulation of Gel air bubbles occurred in the acoustic lens according to Comparative Example 3.

Effects

As described above, acoustic lens 21 according to the present embodiment has a configuration in which an ultrasound radiation surface includes: a first area that is located in a lens center portion and forms a focal point at a position corresponding to a deep portion of an ultrasound beam (corresponding to inner area 21a); and a second area that is located on a lens outer side of the first area and forms a focal point at a position corresponding to a shallow portion of the ultrasound beam (corresponding to outer area 21b), and a focal depth formed by a lens portion of each position of the first area and the second area draws a focal depth profile that becomes continuously shallow from a side of the lens center portion to the lens outer side.

Thus, according to acoustic lens 21 of the present embodiment, an ultrasound image having a wide depth of field and high spatial resolution can be generated. In addition, according to acoustic lens 21 of the present embodiment, a sound pressure peak of a central axis sound pressure can be reduced, and thus, it is possible to transmit a high-power ultrasound beam in an ultrasound inspection.

Moreover, according to acoustic lens 21 according to the present embodiment, unlike acoustic lens 21Y according to related art 2, the valley-shaped portion is not formed at the connecting position between inner area 21a and outer area 21b from the viewpoint of the design concept of the ultrasound radiation surface, and thus, it is possible to suppress the occurrence of an image defect due to accumulation of Gel air bubbles in an ultrasound jelly.

Acoustic lens 21 according to the present embodiment enables obtaining ultrasound probe 20 which has a uniformly sliced beam width from a shallow portion to deep portion, and which includes an inexpensive single-row probe called a 1 D instead of multiple-rows of transducers as 1.25 D, 1.5 D, and 1.75 D and is excellent in penetration. Hence, acoustic lens 21 according to the present embodiment achieves a large improvement effect basically by being applied to ultrasound probe 20 of a single row, but the configuration of acoustic lens 21 according to the present embodiment may be applied to a central row of the multiple-row transducers.

Other Embodiments

The present invention is not limited to the above-described embodiment, and various modified modes may be derived from the above-described embodiment.

For example, in the above embodiment, as an example of acoustic lens 21, a lens form of the convex lens type using a member having the slower sound speed than a living body (e.g., silicone resin) has been described, but acoustic lens 21 according to the present invention is applicable to a concave lens using a member having a faster sound speed than a living body (e.g., polymethylpentene resin).

In addition, in the above embodiment, as an example of acoustic lens 21, an aspect has been described in which a material for forming acoustic lens 21 is the same within the surface of the ultrasound radiation surface, but acoustic lens 21 according to the present invention may be formed of a member having a material for forming acoustic lens 21 that differs in quality within the surface of the ultrasound radiation surface (e.g., a member having a different ultrasound refractive index).

Although embodiments of the present invention have been described and illustrated in detail, the disclosed embodiments are made for purpose of illustration and example only and not limitation. The scope of the present invention should be interpreted by terms of the appended claims.

INDUSTRIAL APPLICABILITY

According to an acoustic lens of the present disclosure, it is possible to generate an ultrasound image having a wide depth of field and high spatial resolution.

What is claimed is:

1. An acoustic lens applied to an ultrasound probe and forming an ultrasound beam by focusing ultrasound transmitted from a piezoelectric transducer, wherein:
   an ultrasound radiation surface of the acoustic lens includes: a first area that is located in a lens center portion and forms a focal point at a position corresponding to a deep portion of the ultrasound beam; and a second area that is located on a lens outer side of the first area and forms a focal point at a position corresponding to a shallow portion of the ultrasound beam, and
   a focal depth formed by a lens portion of each position of the first area and the second area draws a profile that becomes continuously shallow from a side of the lens center portion to the lens outer side.

2. The acoustic lens according to claim 1, wherein the focal depth continuously varies in a non-fixed manner from an end of the second area on the side of the lens center portion to an end of the second area on the lens outer side in the profile.

3. The acoustic lens according to claim 1, wherein the focal depth continuously varies, without discontinuous part, from a lens center of the first area to the end of the second area on the lens outer side in the profile.

4. The acoustic lens according to claim 1, wherein:
   the first area has a spherical shape, and
   the second area has an aspherical shape.

5. The acoustic lens according to claim 1, wherein the first area and the second area are areas adjacent to each other along a slice direction of the ultrasound probe.

6. The acoustic lens according to claim 1, wherein a minimum F value defined by a minimum value among a plurality of the F values at a plurality of the lens portions of the positions of the first area and the second area of the acoustic lens is a value within a range of 5 to 7.

7. The acoustic lens according to claim 6, wherein an F value ratio defined by a value obtained by dividing an F value near a center of the lens of the acoustic lens by the minimum F value is a value within a range of 2.5 to 3.5.

8. An ultrasound probe, comprising the acoustic lens according to claim 1.

9. An ultrasound diagnostic apparatus, comprising the ultrasound probe according to claim 8.

\* \* \* \* \*